United States Patent
Ebina et al.

(10) Patent No.: US 7,732,154 B2
(45) Date of Patent: Jun. 8, 2010

(54) METHODS FOR MEASURING THE INSULIN RECEPTOR α SUBUNIT

(75) Inventors: Yousuke Ebina, Tokushima (JP); Toshiyuki Obata, Tokushima (JP); Eiji Okamoto, Ina (JP)

(73) Assignee: Medical and Biological Laboratories Co., Ltd., Nagoya-Shi, Aichi (JP)

(*) Notice: Subject to any disclaimer, the term of this patent is extended or adjusted under 35 U.S.C. 154(b) by 738 days.

(21) Appl. No.: 10/554,561

(22) PCT Filed: Apr. 15, 2004

(86) PCT No.: PCT/JP2004/005412

§ 371 (c)(1),
(2), (4) Date: Oct. 4, 2006

(87) PCT Pub. No.: WO2004/097414

PCT Pub. Date: Nov. 11, 2004

(65) Prior Publication Data

US 2007/0059784 A1    Mar. 15, 2007

(30) Foreign Application Priority Data

Apr. 25, 2003  (JP) ............... 2003-121955
Dec. 26, 2003  (JP) ............... 2003-433303

(51) Int. Cl.
*G01N 33/573*  (2006.01)
*C12P 21/08*  (2006.01)
*C07K 16/00*  (2006.01)

(52) U.S. Cl. ............... 435/7.4; 530/388.24; 530/389.2

(58) Field of Classification Search .............. None
See application file for complete search history.

(56) References Cited

U.S. PATENT DOCUMENTS 5,719,022 A * 2/1998 Seedorf et al. ............... 435/6

FOREIGN PATENT DOCUMENTS

JP    8-103280 A    4/1996
JP    2003-337131 A    11/2003

OTHER PUBLICATIONS

Song et al. J. Immunol. Nov. 1985;135(5):3354-9.*
Kanezaki, et al., (Biochem Biophys Res Commun. Sep. 26, 2003;309:572-577).*
Rosenzweig et al., (J Biol Chem. Oct. 15, 1990;265(29):18030-10834) (cited on Applicant's IDS of Feb. 15, 2008).*

(Continued)

*Primary Examiner*—Cherie M Woodward
(74) *Attorney, Agent, or Firm*—Townsend and Townsend and Crew LLP

(57) ABSTRACT

Presence of free insulin receptor α-subunit in blood was discovered. Furthermore, methods for measuring the insulin receptor α-subunit was provided, the method comprising the steps of contacting the insulin receptor α-subunit in a blood sample with an antibody recognizing the insulin receptor α-subunit, and detecting the binding between the two. Measurement of the free insulin receptor α-subunit in the blood is useful for evaluating risk factors for diabetes.

In addition, the measurement methods of the present invention showed that concentrations of the free insulin receptor α-subunit in the blood of diabetes or cancer patients are significantly high. Free insulin receptor α-subunit in blood is useful as a marker for diabetes or cancer.

3 Claims, 9 Drawing Sheets

OTHER PUBLICATIONS

Apostolopoulou, C., et al., "Expression of insulin receptor (a-subunit) Mab in FNA biopsies of thyroid nodules," 2002, *Acta Cytologica*, vol. 46(1 Supplement), p. 84.

Frittitta, L., et al., "Structural and functional studies of insulin receptors in human breast cancer," 1993, *Breast Cancer Research and Treatment*, vol. 25(1), pp. 73-82.

Heffetz, D., et al., "Receptor aggregation is necessary for activation of the soluble insulin receptor kinase," 1986, *Journal of Biological Chemistry*, vol. 261(2), pp. 889-894.

Naeser, Peter. "Insulin receptors in human ocular tissues: Immunohistochemical demonstration in normal and diabetic eyes," 1997, *Upsala Journal of Medical Sciences*, vol. 102(1), pp. 35-40.

Nakamura, S., et al., "Localization and synthesis of an insulin-binding region on human insulin receptor," 1990, *Journal of Protein Chemistry*, vol. 9(2), pp. 229-234.

Pezzino, V., et al., "Identification and initial characterization of insulin receptor-like immunoreactivity in human plasma," 1992, *Journal of Clinical Endocrinology and Metabolism*, vol. 74(5), pp. 1116-1121.

Rosenzweig, S., et al., "Identification of retinal insulin receptor using site-specific antibodies to a carboxyl-terminal peptide of the human insulin receptor alpha-subunit up-regulation of neuronal insulin receptors in diabetes," *Journal of Biological Chemistry*, vol. 265(29), pp. 18030-18034, Oct. 15, 1990.

Sesti, G., et al., "Peptide-based radioimmunoassay for the two isoforms of the human insulin receptor," 1995, *Diabetologia*, vol. 38(4), pp. 445-453.

Baron, Andre T. et al.; "Soluble epidermal growth factor receptor (sEGFR/sErbB1) as a potential risk, screening, and diagnostic serum biomarker of epithelial ovarian cancer"; *Cancer Epidemiology, Biomarkers & Prevention* 12:103-113 (Feb. 2003).

Beguin, Yves; "Soluble transferring receptor for the evaluation of erythropoiesis and iron status"; *Clinica Chimica Acta* 329:9-22 (2003).

Frode, Tania Silvia et al.; "Tumour necrosis factor-$\alpha$, interleukin-2 soluble receptor and different inflammatory parameters in patients with rheumatoid arthritis"; *Mediators of Inflammation* 11:345-349 (2002).

Kanezaki, Yoshiko et al.; "Injection of the insulin receptor subunit increased blood glucose levels in mice"; *Biochem Biophys Res. Commun.* 309:572-577 (2003).

Kikuchi, Kunimi et al.; "Saibo seicho inshi receptor to gan idenshi sanbutsu (II) insulin receptor"; *Tanpakushitsu Kakusan Koso (Protein. Nucleic Acid and Enzyme)* 30(13):1388-1393 (1985).

Schaefer, Erik M. et al.; "A new transgenic mouse model of chronic hyperglycemia"; *Diabetes* 43:143-153 (Jan. 1994).

Shimada, Fumio et al.; "Insulin-resistant diabetes associated with partial deletion of insulin-receptor gene"; *The Lancet* 335:1179-1181 (May 19, 1990).

Taira, Masato et al.; "Human diabetes associate with a deletion of the tyrosine kinase domain of the insulin receptor"; *Science* 245:63-66 (Jul. 7, 1989).

Taylor, Simeon I.; "Lllly lecture: Molecular mechanisms of insulin resistance: Lessons from patients with mutations in the insulin-receptor gene"; *Diabetes* 41:1473-1490 (1992).

Hornbeck, P. et al., "UNIT 11.2: Enzyme-Linked Immunosorbent Assays (ELISA) for Detection of Antigens," *Current Protocols in Molecular Biology*, vol. 2, Supplement 10, pp. 11.2.1-11.2.22 (1987).

Li, M., et al., "Decreased Insulin Receptor (IR) Autophosphorylation in Fibroblasts from Patients with PCOS: Effects of Serine Kinase Inhibitors and IR Activators," *The Journal of Clinical Endocrinology & Metabolism*, vol. 87(9), pp. 4088-4093 (Sep. 2002).

Roitt, I., et al., "Immunological Techniques," *Immunology*, 2$^{nd}$ Edition, pp. 25.5-25.6 (1989).

* cited by examiner

SIGNAL PEPTIDE
mgtggrrgaaaapllvavaalllgaag<u>HLYPGEVCPGMDIRNNLTRLHELENCSVIEGHL</u>
-27                          1

<u>QILLMFKTRPEDFRDLSFPKLIMITDYLLLFRVYGLESLKDLFPNLTVIRGSRLFFNYAL</u>

<u>VIFEMVHLKELGLYNLMNITRGSVRIEKNNELCYLATIDWSRILDSVEDNHIVLNKDDNE</u>

<u>ECGDICPGTAKGKTNCPATVINGQFVERCWTHSHCQKVCPTICKSHGCTAEGLCCHSECL</u>

<u>GNCSQPDDPTKCVACRNFYLDGRCVETCPPPYYHFQDWRCVNFSFCQDLHHKCKNSRRQG</u>

<u>CHQYVIHNNKCIPECPSGYTMNSSNLLCTPCLGPCPKVCHLLEGEKTIDSVTSAQELRGC</u>

<u>TVINGSLIINIRGGNNLAAELEANLGLIEEISGYLKIRRSYALVSLSFFRKLRLIRGETL</u>

<u>EIGNYSFYALDNQNLRQLWDWSKHNLTTTQGKLFFHYNPKLCLSEIHKMEEVSGTKGRQE</u>

<u>RNDIALKTNGDKASCENELLKFSYIRTSFDKILLRWEPYWPPDFRDLLGFMLFYKEAPYQ</u>

<u>NVTEFDGQDACGSNSWTVVDIDPPLRSNDPKSQNHPGWLMRGLKPWTQYAIFVKTLVTFS</u>

<u>DERRTYGAKSDIIYVQTDATNPSVPLDPISVSNSSSQIILKWKPPSDPNGNITHYLVFWE</u>

<u>RQAEDSELFELDYCLKGLKLPSRTWSPPFESEDSQKHNQSEYEDSAGECCSCPKTDSQIL</u>

<u>KELEESSFRKTFEDYLHNVVFVPRKTSSGTGAEDPRPSRKRR</u>slgdvgnvtvavptvaaf
                                          736 pntsstsvptspeehrpfekvvnkeslvisglrhftgyrielqacnqdtpeercsvaayv sartmpeakaddivgpvtheifennvvhlmwqepkepngliv1yevsyrrygdeelhlcv SspI
srkhfalergcrlrglspgnysvriratslagngswteptyfyvtdyldvpsniak|iiig
plifvflfsvvigsiylfl|rkrqpdgplgplyassnpeylsasdvfpcsvyvpdewevsr ekitllrelgqgsfgmvyegnardiikgeaetrvavktvnesaslrerieflneasvmkg ftchhvvrllgvvskgqptlvvmelmahgdlksylrslrpeaennpgrppptlqemiqma aeiadgmaylnakkfvhrdlaarncmvahdftvkigdfgmtrdiyetdyyrkggkgllpv rwmapeslkdgvfttssdmwsfgvvlweitslaeqpyqglsneqvlkfvmdggyldqpdn cpervtdlmrmcwqfnpkmrptfleivnllkddlhpsfpevsffhseenkapeseeleme fedmenvpldrsshcqreeaggrdggsslgfkrsyeehipythmnggkkngriltlprsn ps (SEQ ID NO:2)

FIG. 2

METHODS FOR MEASURING THE INSULIN RECEPTOR α SUBUNIT

TECHNICAL FIELD

The present invention relates to methods for measuring a free insulin receptor α-subunit in blood. The present invention also relates to methods for diagnosing diabetes and cancer.

BACKGROUND ART

Insulin is a hormone that plays an important role in the metabolic regulation of glucose, an energy source for living organisms. Produced in pancreatic Langerhans β cells, insulin acts on cells carrying insulin receptors and promotes the uptake of glucose by these cells. The blood-sugar level in the body is maintained within an appropriate range by the function of insulin. Diabetes is one of the pathological conditions caused by insufficient insulin function due to some cause.

Major causes of insufficient insulin function include abnormal insulin secretion and decreased sensitivity to insulin. The former is called type 1 diabetes mellitus. Since responsiveness to insulin is maintained in type 1 diabetes mellitus, blood sugar level can be controlled by administering insulin. Type 1 diabetes mellitus is also called insulin-dependent diabetes mellitus (IDDM), and is the main cause of juvenile diabetes.

On the other hand, the latter is called type 2 diabetes mellitus. Type 2 diabetes mellitus is also called non-insulin dependent diabetes mellitus (NIDDM), and is the type of diabetes frequently found in adults. In Japan, 95% of diabetes patients are said to have type 2 diabetes mellitus. Since the body's responsiveness to insulin is decreased in these patients, even an insulin administration cannot regulate the blood sugar level. Type 2 diabetes mellitus is thought to develop due to several genetic defects and environmental factors such as obesity, stress, and aging. At present, approximately 7,400,000 type 2 diabetes patients are said to exist in Japan, and the number is increasing with the aging of the population. The number of patients is even predicted to be as many as 16,200,000, when including prediabetes patients. Therefore, the diagnosis and treatment of type 2 diabetes mellitus is an important research issue for the modern society.

To date, the causative gene of type 2 diabetes mellitus has not been revealed. Presumed candidate genes are genes of factors involved in the mechanism of insulin action, or genes of factors involved in insulin secretion. Factors thought to be involved in insulin action are:

insulin receptor,
insulin receptor substrate-1 (IRS-1),
glucose transporter type 4, etc.

Genes of factors predicted to be involved in insulin secretion are:

glucose transporter type 2,
glucokinase,
mitochondrial genes, etc.

For insulin to act on a target cell, it must bind to the insulin receptor present on the target cell membrane. Furthermore, there are many reports of insulin resistance in the early stage of type 2 diabetes (Non-Patent Document 1/Taylor, S. I. Diabetes 41:1473-1490, 1992). In view of these facts, the relationship between insulin receptor abnormalities and diabetes has also been examined. If abnormalities are present in insulin receptor function, strong insulin resistance will arise, resulting in severe diabetes.

Recently, many insulin receptor abnormalities have been discovered by researchers including the present inventors, and it is becoming evident that test results and symptoms of patients vary depending on the type of mutation (Non-Patent Document 2/M. Taira et al., Science 245:63-66, 1989; Non-Patent Document 3/F. Shimada et al., Lancet. 335:1179-1181, 1990). This suggests that a part of the pathogenesis of type 2 diabetes mellitus may be defects in the insulin receptor gene. The present inventors have actually identified one of the polymorphisms that allow genetic diagnosis of type 2 diabetes mellitus, and have already filed a patent application (Patent Document 1/Unexamined Published Japanese Patent Application No. (JP-A) Hei 8-103280).

Insulin receptors are heterotetrameric receptor proteins composed of two subunits, α and β. The α-subunit is present outside the cell and the β-subunit penetrates the cell membrane. The α-subunit is linked to the extracellular domain of the β-subunit via an SS bond through an SH group in a cysteine residue on the C-terminal side thereof.

When insulin binds to the α-subunit, a tyrosine residue in the intracellular domain of the β-subunit is autophosphorylated, and the insulin signal is transmitted to the cell. After binding with insulin, the insulin receptor present in the cell membrane is then taken into the cell by endocytosis (the half-life of the receptor is seven hours). The number of insulin receptors decrease with the increase of insulin concentration. This is called down regulation.

In the polymorphism of insulin receptor found by the present inventors, Thr at position 831 in the β-subunit is mutated to Ala (IRA831). Insulin receptor dysfunction caused by this amino acid substitution has not been confirmed. However, genetic statistics indicated that there is a strong relation between IRA831 and type 2 diabetes mellitus.

Disorders due to receptor abnormalities or the presence of free receptors in blood have recently been reported for some diseases (Non-Patent Document 4/Frode, T. S., Tenconi, P., Debiasi, M. R., Medeiros, Y. S., "Tumour necrosis factor-alpha, interleukin-2 soluble receptor and different inflammatory parameters in patients with rheumatoid arthritis." Mediators Inflamm. 2002 Dec; 11(6): 345-9; Non-Patent Document 5/Baron, A. T., Cora, E. M., Lafky, J. M., Boardman, C. H., Buenafe, M. C., Rademaker, A., Liu, D., Fishman, D. A., Podratz, K. C., Maihle, N. J., "Soluble Epidermal Growth Factor Receptor (sEGFR/sErbB1) as a potential Risk, Screening, and Diagnostic Serum Biomarker of Epithelial Ovarian Cancer." Cancer Epidemiol Biomarkers Prev., 2003 Feb; 12(2): 103-13; Non-Patent Document 6/Beguin, Y "Soluble transferrin receptor for the evaluation of erythropoiesis and iron status." Clin. Chem. Acta., 2003 Mar.; 329(1-2): 9-22). Furthermore, hyperglycemia and hyperinsulinemia have been observed in transgenic mice that release the insulin receptor α-subunit into the blood (Non-Patent Document 7/ERIK M. SCHAEFER et al. DIABETES vol. 43, 143-153; 1994). However, in humans, the presence of free insulin receptors in blood has not been reported.

Substances whose levels in biological samples change with disease states are often useful as diagnostic markers for the diseases. For example, substances in biological samples that can be used as cancer indicators are called tumor markers. When a cancer is present, tumor marker levels in these biological samples change significantly compared to those in healthy subjects. Therefore, based on the measured value of tumor markers, it is possible to estimate the possibility of cancer in the subject. Usually, definite diagnosis of the presence or absence of cancer using only tumor markers is considered difficult. However, measurement of tumor markers is considered effective in screening for test subjects who require more advanced and detailed cancer tests.

Among tumor markers, there are some whose measured levels change in correlation with the size and progression of the cancer. Such tumor markers are useful as indicators for observing therapeutic effects on cancer.

Many tumor markers have been reported so far. Generally, tumor markers are often substances that originally exist in normal tissues. Even in healthy people, the measured level of tumor markers may change due to physiological conditions and diseases other than cancer. Therefore, subjects who do not have cancer may be judged as positive, i.e., "false-positive". Conversely, tumor markers of subjects who should be diagnosed as having cancer may remain within a normal range. In this case, subjects who should be positive are determined as negative, i.e., "false-negative".

Positive or negative judgments are made based on the relationship between the measured tumor marker levels and the cutoff values. More specifically, when using a tumor marker with a measured value that is significantly high in cancer patients, cancer is suspected if the measured value is greater than or equal to a certain value (cutoff value). Generally, if a cutoff value is set high, false-negative will increase and false-positives will decrease. Conversely, lowering the cutoff value decreases false-negatives, but increases false-positives. Since the increase in false-negatives means that some cancers would go undetected, keeping it to a minimum is preferable. On the other hand, increase in false-positives will lead to advanced tests on subjects who do not need such. Therefore, tumor markers that can keep false-negatives and false-positives within an acceptable range are considered more practical.

Permissible false positives and false negatives vary depending on the level of difficulty of the diagnosis, presence or absence of a therapeutic method, or the number of patients of a cancer. In addition, an important criterion is whether or not other tumor markers that should be used for comparison are known. When confirming therapeutic effects or monitoring recurrence in patients known to have cancer, tumor markers are continuously monitored. In such applications, the response characteristics of the marker to cancer are given more weight than the issue of false negativeness or false positiveness. Based on such criteria, several tumor markers have been put to practical use. Examples of currently widely-used tumor markers are as follows:

AFP (liver cancer, kidney cancer, cancer of the digestive system)
CEA (liver cancer, kidney cancer, cancer of the digestive system)
CA19-9 (pancreatic cancer, biliary tract cancer, colon cancer)
CA125 (ovarian cancer)
PSA (prostate cancer)
NSE (small-cell lung cancer)
CYFRA (lung cancer —squamous cell carcinoma—)

Some of these tumor markers have been practically applied for specific types of cancers, and others have been recognized as tumor markers for a relatively wide variety of cancers. For example, NSE, CYFRA, or such are tumor markers for specific types of cancers. On the other hand, AFP, CEA, or such are tumor markers that are positive in a relatively wide variety of cancers.

Tumor markers having low specificity to cancer types and which are applicable as tumor markers for a variety of cancers are particularly referred to as "broad-spectrum tumor markers". Broad-spectrum tumor markers are more advantageous than markers specific to a certain cancer type in that they can be utilized to detect or assess therapeutic effects on a broad range of cancer types. The usability of known broad-spectrum tumor markers such as AFP or CEA as tumor markers has been acknowledged for certain cancer types such as cancers of the liver, digestive system, and kidney. However, their usefulness as tumor markers is not always recognized in other cancer types. Therefore, provision of tumor markers that can cover cancer types that are difficult to diagnose with known tumor markers would be useful.

As mentioned above, presence of free receptors in blood has been reported in some diseases (Non-Patent Documents 4-6). Transgenic mice that release the insulin receptor α-subunit into the blood have also been confirmed to exhibit hyperglycemia or hyperinsulinaemia (Non-Patent Document 7). However, in humans, there are no reports that suggest a relationship between cancer and free insulin receptors in blood. The finding that correlated the insulin receptor α-subunit to cancer is the work of a group at Genentech and Memorial Sloan Kettering Cancer Center in the United States, in February 1985, who cloned the human insulin receptor gene, determined the complete amino acid sequence, and analyzed the amino acid sequence to reveal homologies with the epidermal growth factor (EGF) receptor and the protein of cancer gene src.

DISCLOSURE OF THE INVENTION

An objective of the present invention is to provide methods for measuring free insulin receptor α-subunit present in blood and methods for diagnosing diabetes and cancer.

The present inventors continued to study causes hindering insulin function. As a result, the insulin receptor α-subunit existing in the blood in a free form was revealed to hinder insulin action and cause hyperglycemia. The present inventors thought it necessary to establish a system for measuring the insulin receptor α-subunit in order to advance analyses on the relationship between diabetes and free insulin receptor α-subunit in the living body. Consequently, the present inventors established methods for measuring the free α-subunit in blood, and completed the invention. More specifically, the present invention relates to the following methods for measuring the insulin receptor α-subunit, reagents for the measurement, methods for diagnosing diabetes, and reagents for diagnosing diabetes.

[1] A method for measuring a free insulin receptor α-subunit in blood, wherein the method comprises the steps of:
 (1) contacting a blood sample with an antibody recognizing the insulin receptor α-subunit;
 (2) detecting binding of said antibody to the insulin receptor α-subunit present in blood; and
 (3) determining the amount of free insulin receptor α-subunit in blood based on the level of binding detected between said antibody and subunit.

[2] The method of [1], wherein the antibody recognizing the insulin receptor α-subunit is a first antibody that is bound to a solid phase or comprises a label that can be bound to a solid phase, and the method comprises the step of detecting the insulin receptor α-subunit bound to the first antibody by binding a second antibody recognizing the insulin receptor α-subunit.

[3] A reagent for measuring a free insulin receptor α-subunit in blood, wherein the reagent comprises an antibody recognizing the insulin receptor α-subunit.

[4] A method for diagnosing diabetes, wherein the method comprises the steps of:
 a) measuring the amount of a free insulin receptor α-subunit in a biological sample of a subject;
 b) comparing the amount of the free insulin receptor α-subunit with that of a control; and c) determining the subject to have diabetes when the amount of free insulin receptor α-subunit in the biological sample of the subject is greater than that of the control.

[5] The method for diagnosis of [4], wherein the biological sample is a blood sample.

[6] The method for diagnosis of [5], wherein the amount of the free insulin receptor α-subunit is measured by the method of [1].

[7] A reagent for diagnosing diabetes, wherein the reagent comprises an antibody recognizing a peptide comprising the amino acid sequence of an insulin receptor α-subunit.

The present invention also relates to the use of antibodies in the production of reagents for diagnosing diabetes, where the antibodies recognize peptides comprising an amino acid sequence of the insulin receptor α-subunit. Alternatively, the present invention relates to the use of antibodies in diagnosing diabetes, where the antibodies recognize peptides comprising an amino acid sequence of the insulin receptor α-subunit.

In the process of continuing dedicated research on the role of free insulin receptor α-subunit in the living body, the present inventors measured the insulin receptor α-subunit in sera obtained from various cancer patients, and discovered for the first time that there is a significant difference between the measured values for the various cancer patients and healthy individuals. More specifically, the present inventors found that measuring the insulin receptor α-subunit is useful for cancer diagnosis, and completed this invention. Therefore, the present invention relates to the following methods for diagnosing cancer and reagents for diagnosing cancer.

[8] A method for diagnosing cancer, wherein the method comprises the steps of:

(a) measuring the amount of a free insulin receptor α-subunit in a biological sample of a subject;

(b) comparing the amount of the free insulin receptor α-subunit with that of a control; and (c) determining the subject to have cancer when the amount of the free insulin receptor α-subunit in the biological sample of the subject is greater than that of the control.

[9] The method for diagnosis of the above [8], wherein the biological sample is a blood sample.

[10] The method for diagnosis of [9], wherein the amount of the free insulin receptor α-subunit is measured by the method of [1].

[11] A reagent for diagnosing cancer, wherein the reagent comprises an antibody recognizing a peptide comprising the amino acid sequence of an insulin receptor α-subunit.

The present invention also relates to the use of antibodies in the production of reagents for diagnosing cancers, where the antibodies recognize peptides comprising an amino acid sequence of the insulin receptor α-subunit. Alternatively, the present invention relates to the use of antibodies in diagnosing cancers, where the antibodies recognize peptides comprising an amino acid sequence of the insulin receptor α-subunit.

The present invention provides methods for measuring free insulin receptor α-subunit in blood. Until now, the presence of free insulin receptor α-subunit in blood has not been confirmed. Furthermore, methods for measuring it have not been established. The present inventors elucidated that the free insulin receptor α-subunit in blood obstructs insulin action. Therefore, measuring the free insulin receptor α-subunit in blood is useful for evaluating the risk for diabetes. The present inventors showed that the concentration of the free insulin receptor α-subunit in the blood of diabetes patients was, in fact, significantly high. Therefore, the methods of the present invention are useful as methods for diagnosing diabetes.

The present invention also provides free-form insulin receptor α-subunits, which are useful for measuring free insulin receptor α-subunit, and methods for producing them. The free-form α-subunits obtainable by the present invention can be utilized as standard samples and immunogens.

The present invention further provides novel methods for diagnosing cancer. Until now, there have been no reports proving the relationship between free insulin receptor α-subunit and cancer. The present inventors showed that the amount of free insulin receptor α-subunit in the blood of various cancer patients was significantly elevated as compared to that of healthy individuals. Therefore, the free insulin receptor α-subunits can be utilized as cancer markers.

The present invention provides methods for measuring free insulin receptor α-subunits in blood comprising the following steps:

(1) contacting a blood sample with an antibody recognizing the insulin receptor α-subunit;

(2) detecting binding of said antibody to the insulin receptor α-subunit present in blood; and (3) determining the amount of free insulin receptor α-subunit in blood based on the level of binding detected between said antibody and subunit.

In the present invention, the term "free" means that the molecule is dispersed in blood. Insulin receptors are proteins typically localized on cell membrane surfaces. Furthermore, it has been shown that insulin receptors are highly expressed in skeletal muscles, adipose tissues, liver, brain, and such. In other words, marked expression of the insulin receptor is not observed in blood cells such as lymphocytes. Therefore, it was unknown whether a free insulin receptor α-subunit exists in blood. It was the present inventors who revealed that a free insulin receptor subunit is indeed present in blood.

A method for measuring the insulin receptor was known (Human insulin receptor radioimmunoassay: applicablity to insulin-resistant state. Am. J. Physiol. 257 (Endocrinol. Metab. 20) E451-E457, 1989). However, the existence of free insulin receptor α-subunit in blood was not known, and methods for measuring were not established. There is only one document indicating the possibility of the presence of the α-subunit in blood (J. Clin. Endocrinol. Metab. 1992 May; 74(5):1116-21).

In the present invention, the insulin receptor α-subunit present in blood can be measured by its binding to an antibody that recognizes the insulin receptor α-subunit. Antibodies used in the present invention that recognize the insulin receptor α-subunit can be obtained by known methods. In the present invention, the amount of insulin receptor α-subunit can be measured as concentration in a sample. Needless to say, concentration means the amount per unit volume of the sample.

Antibodies necessary for the present invention can be obtained, for example, by using recombinant insulin receptors as an immunogen. The present inventors demonstrated that the insulin receptor α-subunit could be secreted outside of the cell by using cDNAs encoding amino acid sequences as described below. Secretory polypeptides that can be obtained in this manner, fragments thereof, and such may be utilized as immunogens for obtaining the antibodies of the present invention.

For example, secretory polypeptides comprising the amino acid sequence described in SEQ ID NO: 2, or fragments thereof are useful as antigens for obtaining the antibodies of the present invention. These polypeptides can be obtained by transforming suitable hosts with vectors that harbor cDNA of a known insulin receptor α-subunit or the nucleotide sequence of SEQ ID NO: 1 (or fragments thereof) in an expressible manner. Polynucleotides comprising the nucleotide sequence of SEQ ID NO: 1 encodes the amino acid sequences constituting the region of the signal peptide (−27 to −1), α-subunit (1-735), and a part of the β-subunit (736-926) in the human insulin receptor protein. The numbers in parenthesis indicate the position of each region in SEQ ID NO: 2.

DNA comprising the necessary nucleotide sequence can be cloned using mRNA prepared from tissues where the insulin receptor α-subunit is expressed. Alternatively, DNA comprising the nucleotide sequence shown in SEQ ID NO: 1 can be obtained by modifying a known nucleotide sequence of the cDNA of an insulin receptor α-subunit. Recombinant insulin receptor α-subunits expressed in this manner are preferred as immunogens for obtaining antibodies to be used in this invention.

Antibodies to be used for measuring the insulin receptor α-subunit can be obtained by using polynucleotides that hybridize under stringent conditions with the DNA comprising the nucleotide sequence of SEQ ID NO: 1 and encode a secretory polypeptide immunologically equivalent to the insulin receptor α-subunit, or polynucleotides that have 90% or greater homology with the nucleotide sequence of SEQ ID NO: 1 and encode a secretory polypeptide having immunologically equivalent to the insulin receptor α-subunit, to acquire immunogenic polypeptides.

Alternatively, domain peptides of the insulin receptor α-subunit can be used as an immunogen. Domain peptides used as an immunogen can be easily synthesized using a peptide synthesizer. Synthetic peptides can be prepared as immunogens by linking them to carrier proteins.

The maleimidobenzoyl-N-hydrosuccinimide method (hereinafter abbreviated as the MBS method) and such are generally used to link synthetic peptides to carrier proteins. Specifically, a cysteine is introduced into a synthetic peptide, and the peptide is cross-linked to KLH by the MBS method through the cysteine's SH group. The cysteine residue may be introduced at the N terminus or C terminus of the synthesized peptide. As carrier proteins, a suitable protein other than KLH, such as bovine serum albumin may be used. KLH is one of the preferred carrier proteins because of its high immunogenicity.

Immunogens obtained in this manner are mixed with suitable adjuvants, and used to immunize animals. Known adjuvants include Freund's complete adjuvant (FCA) and incomplete adjuvant. The immunization is repeated with appropriate intervals until an increase in antibody titer is confirmed. There are no particular limitations on the animals to be immunized in the present invention. Specifically, mice, rats, rabbits, or such animals commonly used for immunization may be used.

When obtaining the antibodies as monoclonal antibodies, animals that are advantageous for producing them may be used. For example, in mice, many myeloma cell lines for cell fusion are known, and techniques capable of establishing hybridomas with a high probability have already been developed. Therefore, mice are one of the preferable animals for immumization.

Furthermore, immune treatment is not limited to in vivo treatment. Methods for immunologically sensitizing cultured immunocompetent cells in vitro can also be employed. Antibody-producing cells obtained by these methods are transformed and cloned. The method for transforming antibody-producing cells to obtain monoclonal antibodies is not limited to cell fusion. For example, methods for obtaining transformants that can be cloned via virus infection are known.

Hybridomas that produce monoclonal antibodies to be used for the present invention can be screened based on their reactivities to various antigens. Specifically, antibody-producing cells are first selected by using, as an indicator, their binding activities toward the insulin receptor α-subunit or its domain peptides that were used as antigens. Positive clones selected by this screening are subcloned as necessary.

After culturing the established hybridomas under suitable conditions, produced antibodies are collected to yield monoclonal antibodies to be used in the present invention. When the hybridomas are homohybridomas, they can be cultured in vivo by inoculating them intraperitoneally to syngeneic animals. In this case, monoclonal antibodies are collected as peritoneal fluid. When heterohybridomas are used, they can be cultured in vivo using nude mice as a host.

In vivo cultures, as well as cultures outside the body in appropriate culture environments are generally conducted. For example, basal media such as RPMI 1640 and DMEM are generally used as the media for hybridomas. Animal serum and such additives can be added to these media to maintain the antibody producing ability at a high level. When hybridomas are cultured outside of the body, monoclonal antibodies can be collected as a culture supernatant. The culture supernatant can be collected by separating it from cells after culturing, or, when using a culturing apparatus that applies hollow fibers, it can be continuously collected while culturing.

Monoclonal antibodies collected as peritoneal fluid or culture supernatants are prepared into monoclonal antibodies used in the present invention by separating the immunoglobulin fraction by saturated ammonium sulfate precipitation followed by purification steps including gel filtration and ion exchange chromatography. In addition, if the monoclonal antibodies are IgGs, purification methods based on affinity chromatography with a protein A or protein G column are effective.

On the other hand, to obtain the antibodies used in the present invention as polyclonal antibodies, blood is drawn from individuals whose antibody titer has increased after immunization, and the sera are separated to obtain anti-sera. Immunoglobulins are purified from anti-sera by known methods to prepare the antibodies to be used in the present invention. If immunoaffinity chromatography using insulin receptor α-subunit as a ligand is used in combination with immunoglobulin purification, insulin receptor α-subunit-specific antibodies can be obtained.

The following commercially available antibodies can be used in combination in the measurements of the present invention. Examples of the monoclonal antibodies include anti-human insulin receptor alpha-subunit (Neomarker MS632) (LabVision), anti-human insulin receptor alpha-subunit (IM0365) (Immunotech), and MAB1138 (Chemicon) antibodies. Anti-human insulin receptor alpha-subunit (rabbit) H-78 (Santa Cruz) antibodies and such may be used as the polyclonal antibodies.

When antibodies against the insulin receptor α-subunit contact the insulin receptor α-subunit, the antibodies bind to the antigenic determinants (epitopes) that the antibodies recognize thorough the antigen-antibody reaction. The binding of antibodies to antigens can be detected by various immunoassay principles. Immunoassays can be broadly categorized into heterogeneous analysis methods and homogeneous analysis methods. To keep the sensitivities and specificities of immunoassays at a high level, monoclonal antibodies are preferably used. The present invention's methods for measuring the insulin receptor α-subunit using a variety of immunoassay formats will be described in detail.

First, the method for measuring the insulin receptor α-subunit using heterogeneous immunoassays will be described. In heterogeneous immunoassays, mechanisms for separately detecting insulin receptor α-subunit-bound and -unbound antibodies are required.

To facilitate the separation, immobilized reagents are generally used. For example, first, a solid phase onto which antibodies recognizing insulin receptor α-subunit has been immobilized is prepared (immobilized antibody). The insulin receptor α-subunit is bound to this, and then reacted with a labeled second antibody.

When the solid phase is separated from the liquid phase and then washed as necessary, an amount of second antibody proportional to the concentration of insulin receptor α-subunit remains on the solid phase. If the second antibody is labeled, the insulin receptor α-subunit can be quantified by measuring the signal originating from this label.

Any method may be used to bind the antibodies to the solid phase. For example, antibodies can be physically adsorbed to hydrophobic materials such as polystyrene. Alternatively, antibodies can be chemically bound to a variety of materials having functional groups on their surfaces. Furthermore, antibodies labeled with a binding ligand thereof can be bound to a solid phase by trapping the ligand with its binding partner. Combination of a binding ligand and its binding partner includes the avidin-biotin combination or such. The solid phase and antibodies can be conjugated at the same time when reacting the second antibody, or after this reaction.

Similarly, labeling of the second antibody does not have to be direct. More specifically, indirect labeling using binding reactions such as antibodies against antibodies, or avidin to biotin, is also possible.

The concentration of insulin receptor α-subunit in a sample is determined based on the signal intensities measured for standard samples whose insulin receptor α-subunit concentrations are known.

The immobilized antibodies and the second antibodies used for the heterogeneous immunoassays mentioned above may be any, as long as they recognize an insulin receptor α-subunit, or fragments comprising the antigen-binding site. Therefore, monoclonal antibodies, polyclonal antibodies, or a mixture or combination of both may be used. When both antibodies are monoclonal antibodies, combining monoclonal antibodies recognizing different epitopes is preferred.

Since the antigen to be measured is sandwiched by antibodies, such heterogenous immunoassays are called sandwich methods. As sandwich methods excel in measurement sensitivity and reproducibility, they are one of the preferred principles of measurement in the present invention.

The principles of competitive inhibition reactions can be applied to the heterogeneous immunoassays. More specifically, these are immunoassays based on the phenomenon that the insulin receptor α-subunit in a sample competitively inhibits the binding between an antibody and the insulin receptor α-subunit of a known concentration. The insulin receptor α-subunit concentration in the sample can be determined by labeling the insulin receptor α-subunit of known concentration and measuring the amount of the insulin receptor α-subunit that reacted (or did not react) with the antibody.

A competitive reaction system is established by simultaneously reacting, with antibodies, antigens of a known concentration and antigens in a sample. Furthermore, analyses by an inhibitory reaction system are possible when antibodies are reacted with antigens of a known concentration after reacting with antigens in the sample. In both types of reaction systems, reaction systems that are superior in operability can be constructed by preparing either the antibodies or the antigens of known concentration (used as reagent components) as labeled components, and the other as the immobilized reagents.

The labeling components used in such heterogeneous immunoassays include radioisotopes, fluorescent substances, light-emitting substances, substances having enzymatic activity, macroscopically observable substances, and magnetically observable substances. Specific examples of these labeling substances are shown below.

Substances having enzymatic activity:
peroxidase, glucose oxidase,
alkaline phosphatase, lactate dehydrogenase,
urease, catalase, amylase, etc.
Fluorescent substances:
fluorescein isothiocyanate,
tetramethylrhodamine isothiocyanate,
substituted rhodamine isothiocyanate,
dichlorotriazine fluorescein, etc.
Radioisotopes:
tritium,
$^{125}$I,
$^{181}$I, etc.

Of these, enzymes or such non-radioactive labels are among advantageous labels in terms of safety, operability, sensitivity, and such. Enzymatic labels can be linked to antibodies or to an insulin receptor α-subunit by known methods such as the periodate method, or maleimide method.

As the solid phase, beads, inner walls of a container, fine particles, porous carriers, magnetic particles, or such are used. Solids that have been fabricated using materials such as polystyrene, polycarbonate, polyvinyltoluene, polypropylene, polyethylene, polyvinyl chloride, nylon, polymethacrylate, latex, gelatin, agarose, glass, metal, ceramic, or such can be used for these solid phases. Solid materials to whose surface functional groups for chemically binding antibodies and such have been introduced are known. Known linking methods including chemical bonding such as poly-L-lysine or glutaraldehyde treatment, or physical adsorption can be applied for solid phases and antibodies (or antigens).

Although the steps of separating the solid phase from the liquid phase as well as washing steps are required in all heterogeneous immunoassays exemplified herein, these steps can easily be performed using immunochromatography, which is a variation of the sandwich method.

More specifically, antibodies to be immobilized are fixed onto porous carriers capable of transporting a sample solution by capillary action. Then a mixture of a sample comprising the insulin receptor α-subunit and labeled antibodies is migrated through this by capillary action. During this migration, the insulin receptor α-subunit reacts with the labeled antibodies, and when it comes into contact with the immobilized antibodies, is trapped at that position. Labeled antibodies that have not reacted with the insulin receptor α-subunit pass through without being trapped on the immobilized antibodies.

As a result, presence of the insulin receptor α-subunit can be detected using as an indicator the signals of the labeled antibodies remaining at the position of the immobilized antibodies. If the labeled antibodies are preloaded on the upstream in the porous carrier, all reactions will be initiated and completed by simply dropping the sample solution, resulting in the construction of an extremely convenient reaction system. In immunochromatography, labeled components that can be distinguished macroscopically, such as colored particles, can be combined to construct an analytical device that does not even need a special reader.

Next, homogeneous immunoassays will be described. In contrast to the heterogeneous immunoassay method that requires separation of the reaction solution as described above, the insulin receptor α-subunit can also be measured by homogeneous analysis methods. Using the homogeneous analysis method, antigen-antibody reaction products can be detected without separating them from the reaction solution.

A representative homogeneous analysis method is an immunoprecipitation reaction in which antigenic substances are quantitatively analyzed by examining precipitates produced following the antigen-antibody reaction. Polyclonal antibodies are generally used for the immunoprecipitation reaction. When applying monoclonal antibodies, multiple types of monoclonal antibodies that bind to different epitopes of the insulin receptor α-subunit are preferably used. The products of precipitation reaction associated with the immunological reaction can be macroscopically observed, or they can be converted to numerical data by optical measurements.

In contrast to these immunoassay methods utilizing the formation of immunological complexes in liquid phase, methods that perform the reaction in gels are also known. Such examples include Ouchterlony test, SRID method, and immunoelectrophoresis. In these methods of analysis based on reactions in gels, clear precipitation lines can be observed by using multiple types of monoclonal antibodies.

Immunological particle agglutination reaction, which uses as an indicator the agglutination of antibody-sensitized fine particles by antigens, is a common homogeneous analysis method. As in the aforementioned immunoprecipitation reaction, polyclonal antibodies or a combination of multiple types of monoclonal antibodies can be used in this method. Fine particles can be sensitized with antibodies through sensitization with a mixture of antibodies, or they can be prepared by mixing particles that have been separately sensitized with each type of antibody. Fine particles obtained in this manner gives matrix-like reaction products upon contact with the insulin receptor α-subunit. The reaction products can be detected as particle aggregates. Particle aggregation may be macroscopically observed, or may be converted into numerical data through optical measurements.

Immunoassay methods based on energy transfer and enzyme channeling are known as examples of homogeneous immunoassays. In methods utilizing energy transfer, different optical labels that have donor/acceptor relationships are linked to each of a plurality of antibodies recognizing adjacent epitopes on an antigen. When immunological reactions take place, the donor and acceptor come closer to each other and energy transfer occurs, resulting in signal extinction or signals such as changes in fluorescence wavelength. On the other hand, enzyme channeling utilizes a combination of enzymes, which are related in that the reaction product of one enzyme is the substrate of the other, as a label for a plurality of antibodies bound to adjacent epitopes. When the enzymes come close to each other due to immunological reactions, the enzyme reactions are enhanced; therefore their binding can be detected as a change in enzyme reaction rates.

The present invention also provides reagents that comprise antibodies recognizing the insulin receptor α-subunit and that are used for measuring free insulin receptor α-subunit in blood. The presence of free insulin receptor α-subunits in blood is a novel finding made by the present inventors. Therefore, the usefulness of antibodies recognizing the insulin receptor α-subunit as reagents for measuring the free insulin receptor α-subunit in the blood is also a novel discovery. Depending on the assay format, antibodies that constitute the measuring reagent of the present invention can be labeled or bound to a solid phase.

The above-exemplified labeled antibodies (or antigens) and immobilized antibodies (or antigens) that are necessary for the each immunoassay method can be prepared as kits by combining them with an insulin receptor α-subunit standard with a predetermined concentration, a buffer for dilution or washing, and such.

Blood samples are used for the present invention's methods for measuring the insulin receptor α-subunit. Blood samples include whole blood and serum or plasma separated from whole blood. Whole blood can also be used as an analysis sample after disrupting blood cell components. Furthermore, blood samples can be diluted as necessary.

The presence of free-form insulin receptor α-subunits in blood is a novel finding made by the present inventors. The insulin receptor α-subunits in the blood are also found in healthy individuals. However, in experiments using mice, administration of the insulin receptor α-subunit into blood caused hyperglycemia and increase in the amount of insulin secretion. Therefore, insulin receptor α-subunits in blood are important as a risk factor for diabetes (type 2 diabetes mellitus), or as an exacerbation factor of type 2 diabetes mellitus. In addition, the information obtained by measuring the free insulin receptor α-subunit in blood in living bodies would be useful for evaluating the risk of diabetes in subjects.

The present inventors showed that a free form of the insulin receptor α-subunit exists in blood. To measure the free form of the insulin receptor α-subunit by an immunoassay, antibodies recognizing the subunit are necessary. Additionally needed are antigens that are usable as a standard sample and have an antibody reactivity that is similar to that of free insulin receptor α-subunit in the living body. The present invention provides polynucleotides useful for producing insulin receptor α-subunits, which can be used as immunogens for obtaining such antibodies, or as standard samples.

More specifically, the present invention relates to a polynucleotide described in any one of the following (a) to (d), and polypeptides encoded by the polynucleotides.
(a) a polynucleotide comprising the nucleotide sequence of SEQ ID NO: 1
(b) a polynucleotide encoding the amino acid sequence of SEQ ID NO: 2
(c) a polynucleotide that hybridizes with a DNA comprising the nucleotide sequence of SEQ ID NO: 1 under stringent conditions and encodes a secretory polypeptide that is immunologically equivalent to the insulin receptor α-subunit.
(d) a polynucleotide that has 90% or more homology to the nucleotide sequence of SEQ ID NO: 1 and encodes a secretory polypeptide that is immunologically equivalent to the insulin receptor α-subunit.

The polynucleotide comprising the nucleotide sequence of SEQ ID NO: 1 described in (a) encodes amino acid sequences constituting each of the regions described below in the human insulin receptor gene. The position of each of these regions in SEQ ID NO: 2 is shown within parenthesis. Furthermore, the amino acid sequence encoded by the nucleotide sequence of SEQ ID NO: 1 is shown by an underline in FIG. 2.

signal peptide (−27 to 1);
α-subunit (1 to 735); and
a part of the β-subunit (736 to 926)

Those skilled in the art can synthesize such polynucleotides based on the nucleotide sequence shown in SEQ ID NO: 1. Alternatively necessary nucleotide sequences can be obtained from the cDNA of known insulin receptors. For example, in the Examples, a polynucleotide comprising the nucleotide sequence of SEQ ID NO: 1 was obtained by digesting the human insulin receptor gene using restriction enzyme SspI.

The present inventors discovered that when an amino acid sequence in which part of the β-subunit is added to the human insulin receptor α-subunit is expressed, the expression product is efficiently secreted to the outside of the cell. In general, receptor molecules expressed on the cell membrane is difficult to purify because removal of cell membrane components becomes an obstacle. In other cases, the removal of cell membrane components disable the maintenance of the receptor molecule structure. Therefore, expressing the receptor molecule as a secretory protein is a useful production technique.

An objective of the present invention is to produce polypeptides useful as standard samples of the free form of the insulin receptor α-subunit or as immunogens. Recombinant proteins secreted outside the cell can be regarded as free molecules having the same existence form as in living bodies. That is, compared to cell membrane receptor molecules extracted from tissues, the polypeptides of this invention that are expressed as secretory proteins are preferred as standard samples or immunogens.

The polynucleotide of the present invention includes the aforementioned polynucleotide of (c) or (d). In the present invention, immunological equivalence can be determined based on reactivity with antibodies. More specifically, when the reactivity of antibodies against the free insulin receptor α-subunit in the blood is absorbed by a certain protein, this protein can be said to be immunologically equivalent to the free insulin receptor α-subunit in blood. Furthermore, when a certain protein is expressed in suitable host cells, and if that protein is secreted into the culture supernatant of the cells, that protein can be proved to be a secretory protein. Typically, when the insulin receptor gene is expressed in transformants, the receptor molecule is localized on the cell membrane due to the function of the transmembrane domain of the β-subunit, and detecting the α-subunit in the culture supernatant is difficult.

There are no particular limitations on the number of amino acids that are mutated in the protein that is immunologically equivalent to the insulin receptor α-subunit, as long as the immunological equivalence is maintained. Regarding the insulin receptor α-subunit, the number of amino acids to be mutated is usually 100 amino acids or less, preferably 50 amino acids or less, more preferably 30 amino acids or less, and even more preferably 10 amino acids or less. Furthermore, there are no limitations on the site of mutation as long as the immunological equivalence is maintained.

Amino acid mutations may be artificial or naturally-occurring mutations. When substituting amino acids, conservative substitution may be utilized. Generally, to maintain protein function, the amino acid used for the substitution preferably has characteristics similar to those of the amino acid before substitution. This type of amino acid residue substitution is called conservative substitution.

For example, Ala, Val, Leu, Ile, Pro, Met, Phe, and Trp are all categorized as non-polar amino acids, and have characteristics similar to each other. Examples of uncharged amino acids include Gly, Ser, Thr, Cys, Tyr, Asn, and Gln. Examples of acidic amino acids include Asp and Glu. Furthermore, basic amino acids include Lys, Arg, and His. Amino acids that constitute each of these groups respectively have characteristics similar to each other. Therefore, the substitution with another amino acid within the same group is likely to maintain the function of the protein.

Such proteins can be obtained by introducing mutations to the nucleotide sequence of SEQ ID NO: 1. Techniques for introducing mutations into a gene comprising a known nucleotide sequence are well known. Alternatively, a protein comprising a desired amino acid sequence can be prepared by chemical synthesis.

As another method for isolating the aforementioned immunologically equivalent protein, hybridization screening can be utilized. For example, those skilled in the art can easily use a polynucleotide comprising the nucleotide sequence of SEQ ID NO: 1, or a fragment thereof to isolate DNAs highly homologous thereto. Subsequent selection of DNAs that encode proteins immunologically equivalent to the polypeptide comprising the amino acid sequence of SEQ ID NO: 2 from thus—isolated DNAs can also be readily carried out by those skilled in the art.

As described, polypeptides that are encoded by DNAs hybridizing with a DNA comprising the nucleotide sequence of SEQ ID NO: 1 and are immunologically equivalent to the polypeptide comprising the amino acid sequence of SEQ ID NO:2 are also included in the polypeptides of the present invention. Those skilled in the art can appropriately select hybridization stringencies for isolating DNAs encoding the immunologically equivalent polypeptides.

Specific hybridization conditions include, for example, conditions of 5×SSC, in the absence of formamide, at 25° C. Hybridization is preferably performed under conditions of 6× SSC, 40% formamide, at 25° C.; and more preferably under conditions of 5×SSC, 50% formamide, at 40° C. Washing after hybridization is performed for example under conditions of 2×SSC, at 37° C., preferably 1×SSC, at 55° C., and more preferably 1×SSC, at 60° C.

Instead of hybridization screening, the PCR method using oligonucleotides complementary to a portion of the nucleotide sequence of SEQ ID NO: 1 as primers can be applied to isolate the polynucleotide of this invention.

Polynucleotides that can be isolated by hybridization screening or PCR, and encode a polypeptide that is immunologically equivalent to the polypeptide comprising the amino acid sequence of SEQ ID NO: 2, are usually highly homologous to the nucleotide sequence of SEQ ID NO: 1. In the present invention, highly homologous means having sequence identity of at least 20% or more, preferably 30% or more, more preferably 40% or more, even more preferably 60% or more, and yet even more preferably 80% or more, throughout the entire polynucleotide and not just a portion thereof. Algorithms for determining nucleotide sequence homology are known (Takashi Miyata et al "Computer-Assisted Genetic Homology Analysis" (Genetic Research Methods I, Tokyo Kagaku-Dojin)).

The polynucleotides of the present invention can be used, for example, for producing recombinant proteins. *E. coli*, yeast, insect cells, animal cells, and such can be used as hosts for producing the polypeptides of the present invention as recombinant proteins. Suitable vectors are respectively determined according to the host cells. For example, the following expression vectors can be used for each type of host cell.

*E. coli*: pGEX5X-3 (Pharmacia), and such yeast: pYES2 (Invitrogen), and such insect cells: pVL1392 (Invitrogen), and such animal cells: pRc/CMV2 (Invitrogen), and such Methods for introducing these vectors into hosts known by those skilled in the art include biological methods, physical methods, and chemical methods. Biological methods include methods that use virus vectors. Physical methods include electroporation, gene gun, or microinjection. Chemical methods include lipofection, calcium phosphate method, and DEAE-Dextran method.

Recombinant proteins produced in hosts can be purified by a discretionary method. Specifically, methods that utilize ion exchange column, affinity column, and such are generally used. The method for expressing recombinant proteins as fusion proteins with GST or 6× is to facilitate detection and purification are also known.

The polynucleotides of (a) to (d) described above can all be used to express the insulin receptor α-subunit (or an immunologically equivalent polypeptide) as a secretory protein. The extracellularly secreted insulin receptor α-subunit can be easily collected from the culture supernatant. Alternatively, the culture supernatant can be directly used as a standard sample or an immunogen.

For example, standard samples for measuring free insulin receptor α-subunits in blood can be produced as follows. First, the culture supernatant of the aforementioned transformant is collected. The collected culture supernatant, is used as it is, or after purifying the desired expression product, for assaying the expression product amount. When the expression product is purified as a pure protein, the amount of the expression product is determined by measuring the concentration of that protein. Alternatively, if there are any contaminants as in a culture supernatant, the amount of the desired expression product can be determined by isolating the product by various chromatographic techniques or electrophoresis. Once the amount of the expression product is determined, the supernatant or the purified protein can be utilized as a standard sample.

The amino acid sequence of SEQ ID NO: 2 is an amino acid sequence derived from a human insulin receptor. When a polypeptide comprising an amino acid sequence different from this amino acid sequence is used as an expression product, the differences in molecular mass can be corrected based on differences in the amino acid sequences of the two.

In the present invention, a "standard sample of a certain protein" refers to a sample in which the amount of this protein has been determined in advance. Standard samples can be serially diluted as necessary. Signals are measured for these serially diluted samples by the aforementioned immunoassays. The relationship between the concentrations of the protein in the standard samples and the measured signals can be expressed as a standard curve (or a calibration curve). Based on the standard curve made in this manner, the concentration of the substance to be measured in the sample can be determined from signals obtained from actual test samples. Alternatively, by formulating a regression equation based on the measurement results of the serial dilutions, and by assigning the values measured from the test samples, the concentration of the substance to be measured in the sample can be determined.

The present invention also provides methods for diagnosing diabetes, wherein the method comprises the following steps:

a) measuring the amount of a free insulin receptor α-subunit in a biological sample of a subject;

b) comparing the amount of the free insulin receptor α-subunit with that of a control; and c) determining the subject to have diabetes when the amount of free insulin receptor α-subunit in the biological sample of the subject is greater than that of the control.

Alternatively, the present invention provides methods for diagnosing cancer, wherein the method comprises the following steps:

(a) measuring the amount of a free insulin receptor α-subunit in a biological sample of a subject;

(b) comparing the amount of the free insulin receptor α-subunit with that of a control; and (c) determining the subject to have cancer when the amount of the free insulin receptor α-subunit in the biological sample of the subject is greater than that of the control.

The present invention is based on the novel finding that the amounts of the insulin receptor α-subunit found in diabetes and cancer patients are significantly high compared to those of healthy individuals. The insulin receptor is a glycoprotein that binds specifically to insulin, with a large molecular mass of approximately 350,000 to 400,000 and having an α2β2 subunit structure (α: molecular mass of 120,000 to 130,000; and β: molecular mass of 90,000). The insulin receptor has not only insulin-binding activity, but also tyrosine-specific protein kinase activity, and is activated upon binding to insulin and transmits signals into cells. Consequently, insulin receptors are usually localized on the cell membrane in insulin target tissues such as muscles. Although it has been shown that insulin receptors are highly expressed in skeletal muscles, adipose tissues, liver, brain, and such, no marked expression of the insulin receptor had been observed in blood cells such as lymphocytes. Therefore, it was unclear whether or not a free insulin receptor is present in blood.

In the present invention's methods of diagnosis, the amount of free insulin receptor in a biological sample can be measured by the methods described above. In particular, the sandwich method is one of the preferred measurement principles of the present invention due to its excellent measurement sensitivity and reproducibility. Results of measurements are compared to results from a control. Examples of a control in the present invention include the amount of free insulin receptor determined by measuring biological samples from healthy individuals. Healthy individuals include humans who are known to have no diabetes or cancer. Desirably, healthy individuals refer to humans who are known to have no diseases.

In the method of diagnosis of the present invention, biological samples include any sample collected from living bodies. Specifically, blood samples, urine samples, or papillary secretions is included in biological samples. The preferred biological samples of the present invention are blood samples. The present inventors elucidated that a free insulin receptor is present in blood. Blood samples include blood fractions separated from the blood. Specifically, samples such as serum, plasma, or hemolytic samples that can be obtained by disrupting blood cell components are included in biological samples. Methods for preparing these samples are known. For example, the methods of diagnosis of the present invention can be carried out using blood samples prepared from blood collected from subjects. Furthermore, blood samples may be diluted as necessary.

The present invention also provides methods of testing for diabetes or cancer, the methods comprising the steps of (1) measuring a concentration of the free insulin receptor α-subunit in blood samples collected from living bodies, and (2) comparing the values to that of the control. If the measured value is shown to be significantly higher as a result of the comparison with the control, there is a high probability that the subject has diabetes or cancer.

For example, as a result of the comparison between the two, if the level of the free insulin receptor α-subunit in the subject is higher than in the healthy individual, the subject is determined to have diabetes or cancer. In order to compare the amount of free insulin receptor α-subunit, a standard value is typically set, for example, based on the above-mentioned amount of free insulin receptor α-subunit in healthy individuals. Based on this standard value, a given range is set as a permissible range. In general, the permissible range is set as ±2 S.D. to ±3 S.D. from the standard value. In the present invention, a high measured value as compared to the control serves as an indicator. Therefore, the maximum value of the settled permissible range is used as the criterion for judgment. This value is called a cutoff value.

In general, techniques for statistically setting the standard value and permissible range based on the value measured for a substance that serves as a marker are known. If the amount of the free insulin receptor α-subunit in a subject shows a value higher than the permissible range (cutoff value), that subject is predicted to have diabetes. When the value is within the permissible range, or is less than the permissible value, there is little possibility of diabetes or cancer.

Alternatively, whether a subject has risk factors for diabetes or not can be predicted based on the present invention. As indicated in the Examples, the presence of free insulin receptor α-subunit in the blood is a risk factor for diabetes. Therefore, even if the subject does not have diabetes, higher measured value of the free insulin receptor α-subunit in the blood than in the control predicts that the subject has a risk factor for diabetes. Prediction of risk factors is included in the diabetes diagnosis of the present invention.

In the method of diagnosis of cancer according to the present invention, a subject is determined to have cancer when the amount of free insulin receptor α-subunit in the subject is higher than in healthy individuals. In the present invention, the types of cancer to be diagnosed are not limited. As shown in the Examples, the amount of the free insulin receptor α-subunit marked significantly high values in biological samples of a variety of cancer patients. Therefore, when the method of diagnosis of the present invention determines that there is a possibility of cancer, it indicates that some type of cancer may be present regardless of the organ where it is present. Cancer in the present invention may be in the primary focus or metastatic focus. Furthermore, cancer in the present invention is also not limited to solid cancers. However, preferable cancers include solid caners. For example, cancers that develop in the lungs, esophagus, pancreas, colon, breast, liver, rectum, or skin can be diagnosed by the present invention.

The present invention also provides reagents for diagnosing diabetes or cancer, the reagents comprising an antibody that recognizes peptides comprising the amino acid sequence of the insulin receptor α-subunit. The usefulness of the free insulin receptor α-subunit in the blood for diagnosing diabetes or cancer is a novel finding made by the present inventors. The antibodies constituting the diagnosis reagents of this invention can be labeled, or linked to a solid phase, depending on the above-mentioned assay format.

In the present invention, antibodies that recognize peptides comprising the amino acid sequence of the insulin receptor α-subunit include, for example, antibodies that recognize peptides comprising a continuous amino acid sequence selected from the amino acid sequence of SEQ ID NO: 2. Typically, antibodies are said to recognize antigenic determinants composed of an amino acid sequence of three or more amino acid residues. The preferred length of an amino acid sequence recognized by the antibodies of the present invention is typically three or more, preferably five or more, for example, 7 to 20 amino acid residues. Peptides of eight to nine amino acid residues generally can constitute antigenic determinants unique to the protein.

Labeled antibodies (or antigens) and immobilized antibodies (or antigens) necessary for various immunoassay methods exemplified in the present description can be prepared as a kit by combining them with the insulin receptor α-subunit standard whose concentration has been examined, a buffer to be used for dilution or washing, and such.

All prior art references cited herein are incorporated by references into the present description.

BRIEF DESCRIPTION OF THE DRAWINGS

FIG. 2 shows the amino acid sequences of each subunit in the amino acid sequence of the insulin receptor precursor protein, and the relationship with the amino acid sequence of the recombinant expressed in the Examples. In the figure, capital letters indicate α-subunit, and the amino acid sequences shown in lower-case letters at the N-terminal and C-terminal side of the α-subunit are those of the signal peptide and β-subunit, respectively. In the amino acid sequence of the β-subunit, the boxed portion is the transmembrane (TM) region. The amino acid sequence encoded by the SspI-digested fragment shown in FIG. 1 is underlined.

BEST MODE FOR CARRYING OUT THE INVENTION

Hereinafter, the present invention will be described more specifically with reference to Examples.

Figure 1:
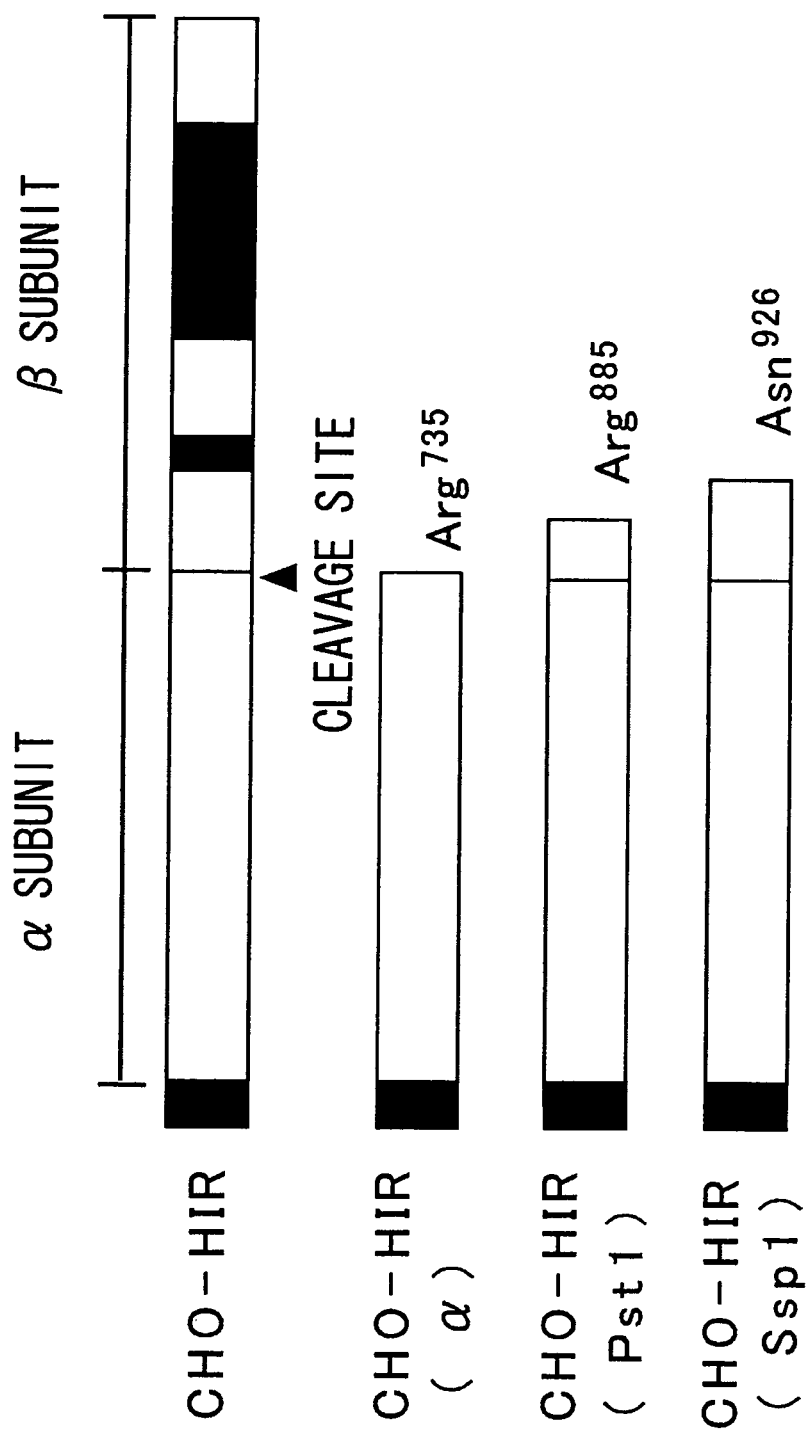
FIG. 1 is a diagram showing the relationship between amino acid sequences encoded by the cDNAs used for expressing the insulin receptor α-subunit in CHO cells in the Examples, and the full-length amino acid sequence of the insulin receptor.

1. Construction of Human Insulin Receptor α-subunit cDNA cDNA for causing secretion of insulin receptor α-subunit into the culture supernatant from CHO cells were constructed. The structures of the cDNAs constructed in the present example are shown in FIG. 1. Each of the cDNAs was obtained by using pcDL1-HIR717 (Ebina et al. Cell. 40, 747-758, 1985) comprising the full-length cDNA (NM_000208) of the human insulin receptor and digesting it at different positions. Each of the cDNAs has the following structures, respectively.

CHO-HIR: insulin receptor α-subunit+β-subunit
CHO-HIR(α): insulin receptor α-subunit alone
CHO-HIR(PstI): α-subunit and amino acids 1 to 150 in the N terminal side of the β-subunit
CHO-HIR(SspI): α-subunit and amino acids 1 to 191 in the N terminal side of the β-subunit The β-subunit transmembrane domain is in positions 195 to 217 from the N-terminal side. This means that CHO-HIR(PstI) and CHO-HIR(SspI) both include a portion of the β-subunit, but lack the transmembrane domain. In FIG. 2, the boxed part within the β-subunit amino acid sequence (the C-terminal side part in lower-case letters) corresponds to the transmembrane region.

Each of the cDNAs was inserted into the animal cell expression vector pCXN2 to obtain expression plasmids of the hIR (human insulin receptor) and its variants. Each restriction enzyme was purchased from Takara (Otsu, Japan) and New England BioLabs (Beverly, Mass.).

2. Culturing and Gene Transfer

Chinese hamster ovary (CHO) cells were cultured in a 5% $CO_2$ incubator using F-12 Nutrient Mixture (Ham's F-12, Invitrogen, Carlsbad, Calif.) media. 10 μg of each expression plasmid obtained in 1 was linearized using the restriction enzyme ScaI, and this was introduced into CHO cells by electroporation with 0.5 μg of blasticidin (pSV2-bsr, Funakoshi, Tokyo, Japan). 24 hours after transfection, the medium was changed to 10 μg/mL blasticidin-resistant F-12 medium, and two weeks later, the remaining colonies were isolated. Expression of hIR was confirmed by polyacrylamide electrophoresis and Western blotting using anti-IRa antibodies.

3. Purification of the α-subunit

Clones showing high expression were amplified in F-12 medium containing 10% FCS, and cultured in 150-mm cell culture dishes (Corning). After culturing to 100% confluency, the cells were washed three times with HEPES buffer [20 mM HEPES (pH 7.4), 140 mM NaCl, 5 mM KCl, 2.5 mM $MgCl_2$, and 1 mM $CaCl_2$] and the medium was exchanged with 20 mL of serum-free medium (CHO-S-SFM II DPM, Invitrogen) per dish.

After culturing for four days, the medium was collected, cell components were removed by centrifugation (1,300×g, 10 minutes, 4° C.), and then the supernatant was collected. 6 μL (50% suspension) of wheat germ lectin (WGA) agarose (Amersham) was added per 1 mL of the supernatant, and this was rotated at 4° C. for two hours for adsorption. The agarose was washed five times. The first and fifth washes were carried out using HEPES buffer [50 mM HEPES (pH 7.4), 150 mM NaCl, 1% Triton X-100]. The salt concentration of the washing solution for the second to fourth washes was set to 500 mM. The adsorbed protein was eluted using HEPES buffer containing 0.2 M N-acetylglucosamine. The eluted sample was added to anti-insulin receptor antibody (α-subunit antibody, Immunotech 0365) column (bed volume; 0.5 mL) and allowed to adsorb while rotating at 4° C. for one hour. The column was washed three times with ten times the bed volume of HEPES buffer, and in this case as well, the salt concentration for the second wash was increased to 500 mM. Using sodium borate buffer containing 1.5 M $MgCl_2$, 200-μL fractions were collected.

Figure 3:
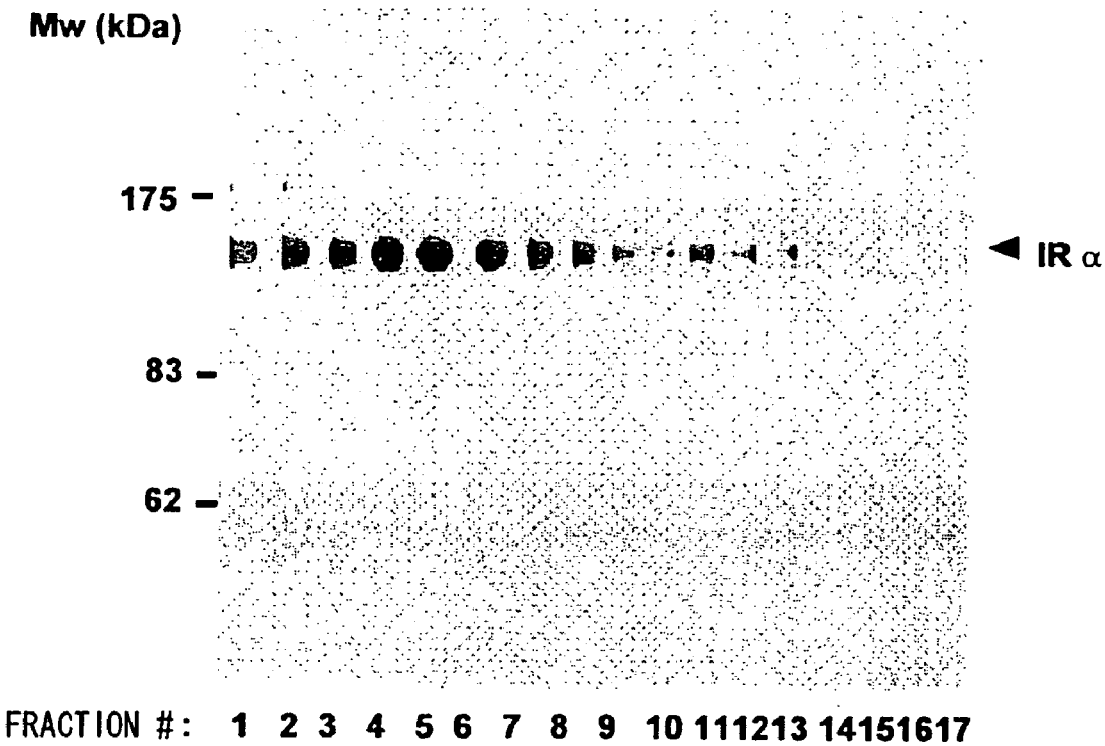
FIG. 3 is a photograph showing the purification result of the insulin receptor α-subunit using an anti-insulin receptor α-subunit antibody column. The insulin receptor α-subunit adsorbed to the anti-insulin receptor antibody (α-subunit antibody, Immunotech 0365) column was eluted using sodium borate buffer containing 1.5 M $MgCl_2$, and the eluate was collected as 200-μL fractions. From each fraction, 20 μL was withdrawn and subjected to 7.5% SDS-PAGE and then silver stained.

The degree of purification of the insulin receptor α-subunit in each fraction was evaluated as follows. First, 20 μL of each fraction was withdrawn and subjected to 7.5% SDS-PAGE and silver staining. A photograph of the stained gel is shown in FIG. 3. A protein having a molecular mass corresponding to the insulin receptor α-subunit was confirmed to be isolated as a nearly pure protein (the band indicated as IRα). The stained gel was scanned with a transmission scanner and evaluated using NIH image software. The protein concentration was determined by the Bradford method using Protein Assay Dye Reagent (BioRad, Hercules, Calif.) with BSA as the standard.

4. Production of Anti-human Insulin Receptor α-subunit Antibodies

Using the purified human insulin receptor α-subunit, rabbits (Japanese white rabbits, female, 3.5 kg) were immunized subcutaneously (at approximately ten sites, once a week). After five immunizations, a small amount of blood was collected from the ear veins, and the serum was separated to check the antibody titer by ELISA.

First, human insulin receptor α-subunit was dissolved in 1/100 M physiological phosphate-buffered saline (PBS) to prepare a 0.1 mg/mL solution, and 100 μL aliquots of this solution was added to Nunc 96-well microplates "Maxisorp". After letting this stand at room temperature (20 to 25° C.) for three hours, the solution inside the wells were removed by suction, and 30 μL of PBS containing 5% bovine serum albumin was added. This was left undisturbed for approximately 18 hours at 4° C., and the unreacted parts in the cups were blocked. After removing the blocking solution, this plate was washed three times with 300 μL of PBS and used as the plates for ELISA.

Antiserum diluted with PBS was further diluted to produce a series of dilutions. 100 μL of the diluted serum was added to each well of the ELISA plate. After leaving this undisturbed at room temperature (20 to 25° C.) for one hour, the reaction solution was removed, and then the plate was washed four times with 30 μL of PBS. Next, 100 μL of the diluted peroxidase-labeled anti-rabbit IgG (Medical and Biological Laboratories Co., Ltd.) was added. After letting this react while standing at room temperature (20 to 25° C.) for one hour, washing was done four times with 30 μL of PBS.

Figure 4:
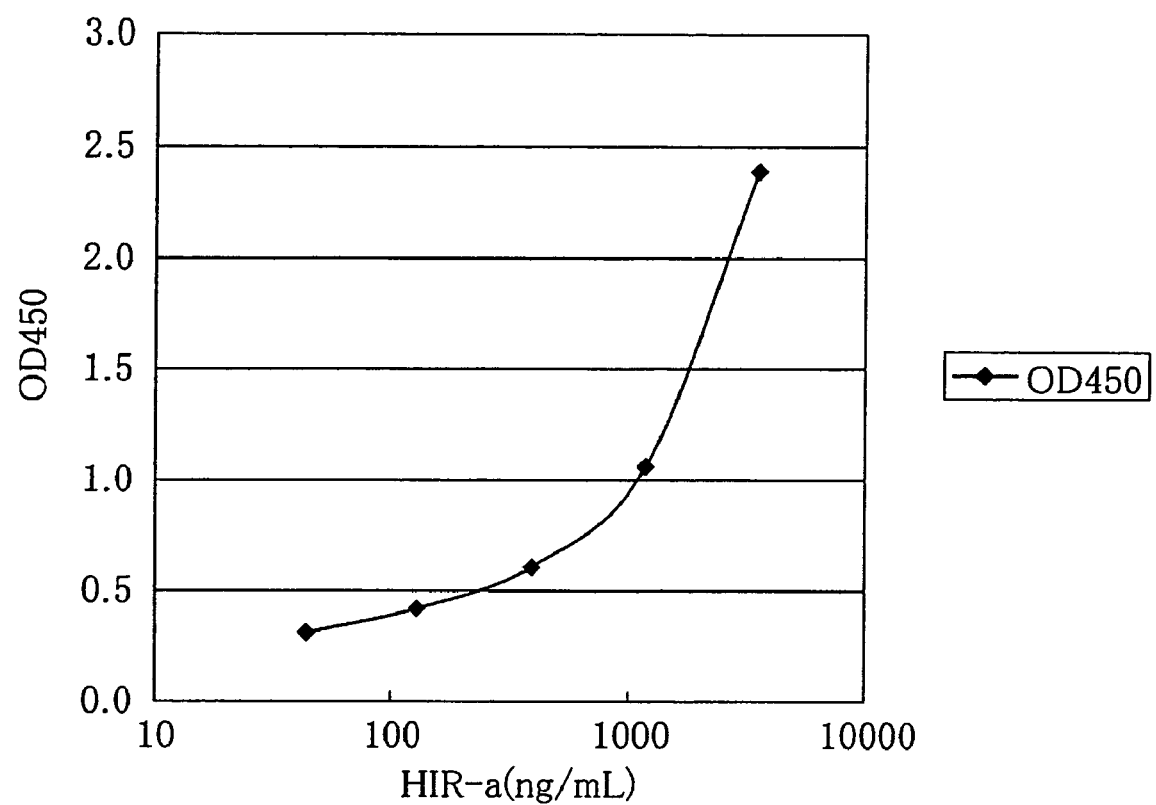
FIG. 4 is a graph showing the standard curve prepared in the Examples for the insulin receptor α-subunit. In the figure, the vertical axis indicates the absorbance at 450 nm, and the horizontal axis indicates the concentration of the insulin receptor α-subunit (ng/mL) in the sample.

100 μL of a solution of 3,3',5,5'-tetramethylbenzidine with hydrogen peroxide was added to the washed wells as the chromogenic substrate. After letting this react for a certain length of time, 1 N sulfuric acid was added to stop the reaction, and the absorbance at wavelength of 450 nm was measured. The results of the measurements are shown in the graph of FIG. 4. As is clear from this result, the obtained antiserum exhibited sufficient antibody titer. From rabbits that showed sufficient antibody titer in this manner, 70 mL of blood was collected from the ear veins and approximately 30 mL of antiserum was obtained. Furthermore, from the polyclonal solution obtained in this manner, IgG fraction was purified using a DEAE cellulose column.

5. Preparation of Labeled Antibodies

Anti-rabbit IgG monoclonal antibodies (2B9 5 µg/mL) dissolved in 0.1 M carbonate buffer (pH 8.5) and NHS-LC-BIOTIN (PIERCE, 25 µg/mL) were mixed and stirred at room temperature for four hours using a stirrer. IgG and NHS-LC-BIOTIN were mixed at a mole ratio of 1:60. After stirring, this solution was dialyzed against physiological phosphate buffered saline (PBS) to obtain biotin-labeled antibodies.

6. Construction of an ELISA System for the Human Insulin Receptor α-subunit

Anti-human insulin receptor α-subunit antibodies were diluted and prepared to a concentration of 40 µg/mL to 80 µg/mL with 0.1 M carbonate buffer (pH 9.6). 100-µL aliquot of the diluted antibody solution was placed into each well of a 96-well microplate (NUNC, Immuno Break Apart Modules Maxisorp #473768). The microplate was left to stand overnight in a humid container at 2 to 8° C. to bind the antibodies.

After incubation, the antibody solution was discarded, and the plate was washed twice with PBS. Excess moisture was removed, and blocking solution (PBS containing 1% BSA and 0.1% $NaN_3$) was added in 200-µL aliquote per well. Blocking was carried out by placing the microplate in a humid container overnight at 2 to 8° C. After blocking, the blocking solution was discarded and excess moisture was removed. Furthermore, the plates were air-dried, and were stored until use in an aluminum-coated bag with a drying agent.

7. Evaluation of the ELISA System

The purified human insulin receptor α-subunit was diluted with a sample dilution buffer (20 mM Tris-HCl, 150 mM NaCl, 1% BSA, 10% normal mouse serum, 25 mg/mL MAK33, 0.1% $NaN_3$, 1% bovine y-globulin, 0.056% Tween 20, pH 7.5) and used as standards. Samples were two-fold diluted with the sample dilution solution and placed into each well of the antibody-sensitized microplate in 100-µL aliquots, and this was allowed to react for three hours at room temperature to form antibody-antigen complexes.

After the reaction, the wells were washed five times with a washing buffer (PBS+0.05% Tween 20). Excess moisture was removed, then 100-µL aliquots of the biotin-labeled antibody diluted with the sample dilution buffer was added to each well, and this was allowed to react at room temperature for three hours. After the reaction, the wells were washed five times using the same washing buffer. After removing excess moisture, avidin-labeled peroxidase diluted with avidin HRP dilution buffer (20 mM Tris-HCl, 150 mM NaCl, 1% BSA, 0.15% Proclin, pH 7.5) was added to each well in 100-µL aliquots, and this was allowed to react at room temperature for three hours. These reactions lead to the formation of an antibody/antigen/biotinylated antibody/avidin-labeled peroxidase complex.

The reacted wells were washed five times with the washing buffer. After removing excess moisture, 100 µl of TMB chromogenic substrate (MOSS, TMBH-100) was added per well. After letting this react at room temperature for approximately 20 minutes for color development, 100 µL of 1 N sulfuric acid was added per well to stop the color development. After this, absorbance was measured at wavelength of 450 nm. The concentration of insulin receptor α-subunit in the samples was read from the calibration curve prepared from the absorbance of the standards. The ELISA system constructed as described above was confirmed to be able to measure the insulin receptor α-subunit.

8. Effects of Administering the Insulin Receptor α-subunit

Eight to ten-week old male mice were fasted for 16 hours and anesthetized using pentobarbital. Next, 100 ng of the purified insulin receptor α-subunit was administered from the cervical vein. The insulin receptor α-subunit was administered in a form dissolved in 50 µL of physiological saline containing 0.1% BSA. Blood was withdrawn from insulin receptor α-subunit-administered mice at various time points through the tail vein, and the blood sugar level was measured. As a control, 50 µL of physiological saline containing 0.1% BSA alone was administered to mice in the same manner.

Figure 5:
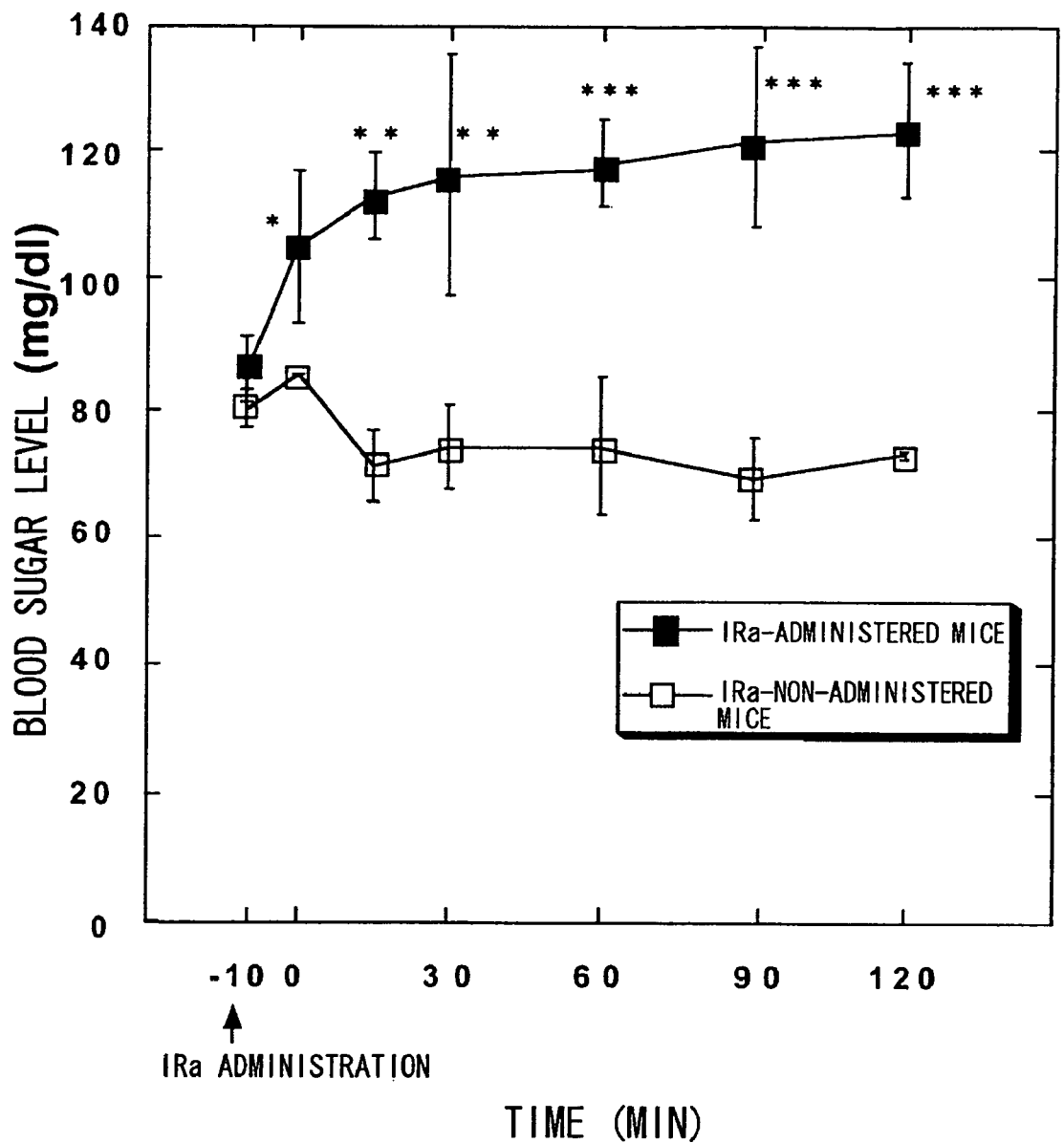
FIG. 5 is a graph showing over-time changes in blood glucose level in mice to which the insulin receptor α-subunit has been administered. In the figure, the vertical axis indicates the blood glucose level (mg/dL), and the horizontal axis indicates the time elapsed (in minutes) where the time of insulin receptor α-subunit administration is set as −10.

The results are shown in FIG. 5. The blood sugar level in the control mice gradually decreased due to continued fasting. On the other hand, in mice that received the insulin receptor α-subunit administration into the blood, over-time increase in the blood glucose level was observed. This may have occurred as a result of the binding of the administered insulin receptor α-subunit with insulin, which inhibited insulin action.

9. Effects of Insulin Receptor α-subunit Administration (Glucose Loading)

Ten minutes after administering the insulin receptor α-subunit under the same conditions as in 7, glucose (2 g/kg body weight) was administered intraperitoneally. After glucose administration, blood was collected from the tail vein at different time intervals, and the blood sugar levels were measured. As a control, the same amount of glucose was administered to mice that had been given only physiological saline containing 0.1% BSA (50 µL) by the same method.

Figure 6:
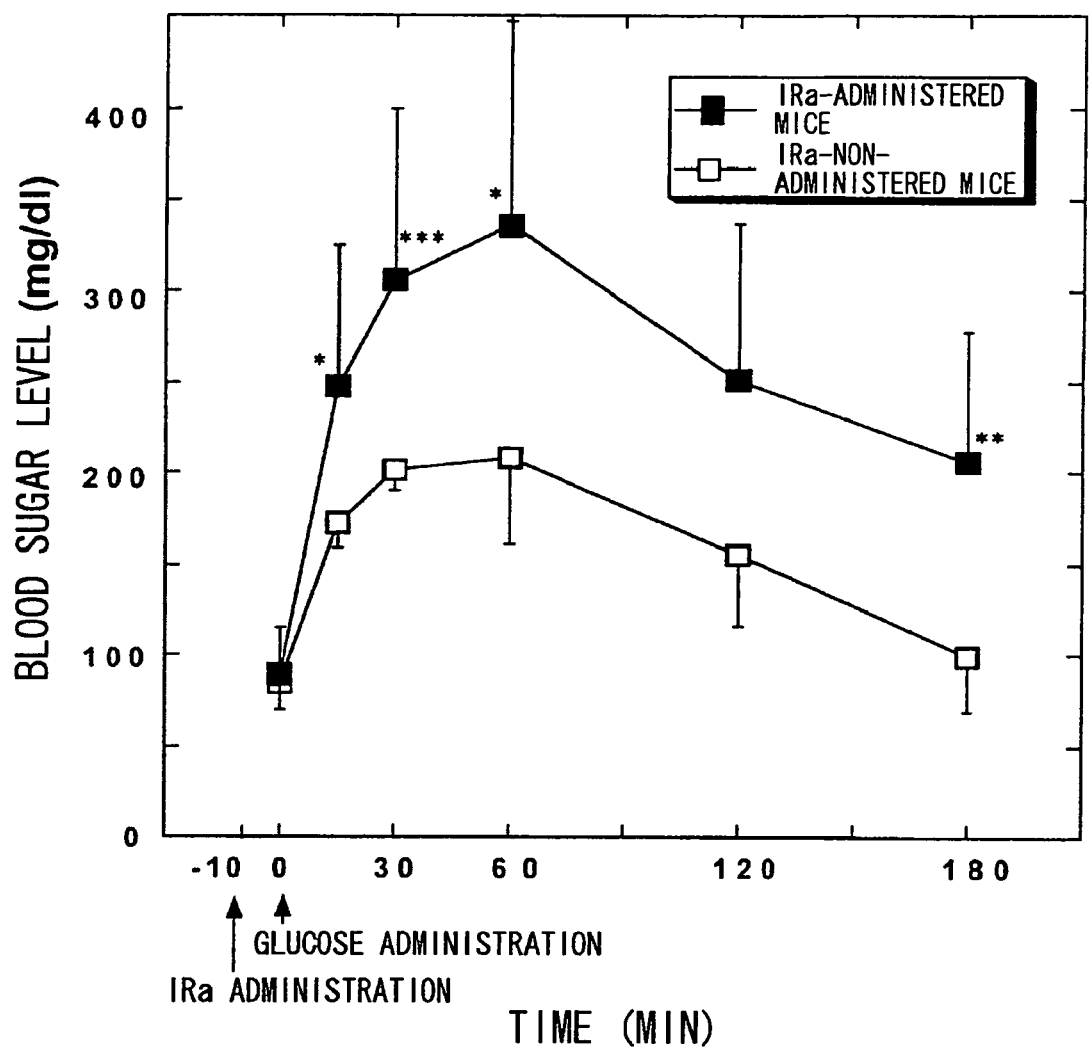
FIG. 6 is a graph showing the over-time changes in blood glucose level in mice to which a glucose load has been given 10 minutes after administration of the insulin receptor α-subunit. In the figure, the vertical axis indicates the blood glucose level (mg/dL), and the horizontal axis indicates the time elapsed (in minutes) where the time of insulin receptor α-subunit administration is set as −10.

The results are shown in FIG. 6. Abnormal glucose tolerance was confirmed in glucose tolerance tests upon administration of insulin receptor α-subunit. These two results indicate that when the insulin receptor α-subunit exists in blood, it is very likely to act as an exacerbation factor for diabetes through its binding to insulin to inhibit insulin action and increase blood glucose level.

10. Measurement of the Insulin Receptor α-subunit in the Sera of Diabetes Patients Two types of monoclonal antibodies (mice) against the human insulin receptor α-subunit were used to develop a sandwich ELISA system for measuring the insulin receptor α-subunit in blood.

Following the above-mentioned method, labeled antibodies were produced using monoclonal antibodies. Anti-α-subunit monoclonal antibody (IM0365) (5 µg/mL) dissolved in 0.1 M carbonate buffer (pH 8.5) and NHS-LC-BIOTIN (PIERCE, 25 µg/mL) were mixed and stirred at room temperature for four hours using a stirrer. IgG and NHS-LC-BIOTIN were mixed at a mole ratio of 1:60. After stiring, this solution was dialyzed against physiological phosphate buffered saline (PBS) to obtain biotin-labeled antibodies.

Similarly, monoclonal antibodies were used to prepare a solid phase plate. Anti-α-subunit monoclonal antibody (Neomarker MS632) was dissolved in 0.1 M carbonate buffer (pH 9.6) at a concentration of 10 µg/mL, and 100 µL of this solution per well was used for sensitization at 4° C., overnight. 200 µL/well of PBS+1% BSA was added for two-hour blocking at room temperature, then the plate was air-dried, sealed, and stored.

These antibodies were used to measure the concentration of the insulin receptor α-subunit in a sample according to the measurement conditions described above.

Figure 7:
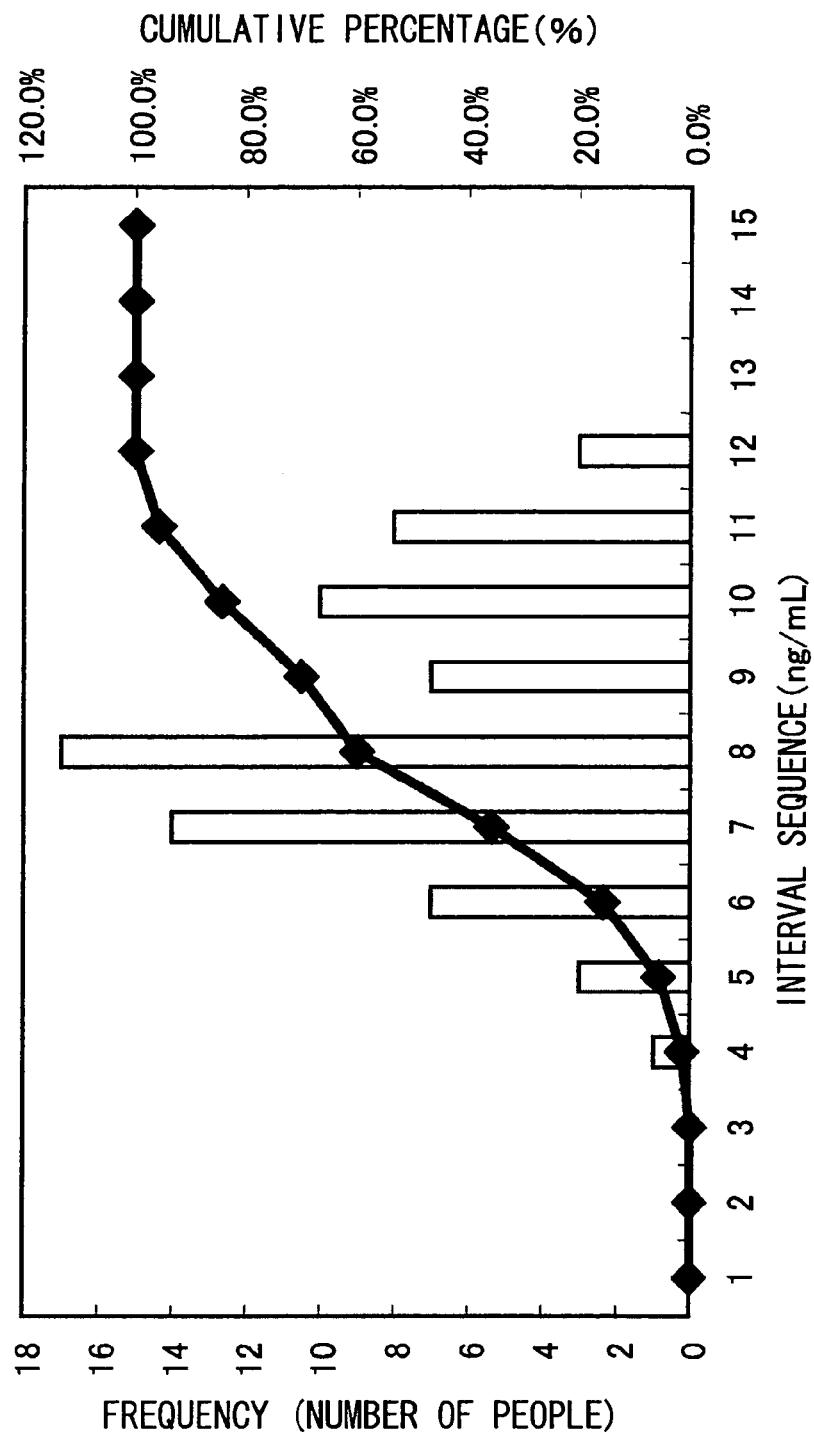
FIG. 7 is a graph showing the distribution of the measured values of the insulin receptor α-subunit in 70 healthy subjects. In the figure, the vertical axis indicates the frequency (number of people) or the cumulative percentage (%) at each measurement level (ng/mL), and the horizontal axis indicates the concentration of the insulin receptor α-subunit.

Among the sera donated by students at University of Tokushima School of Medicine, samples from individuals having a family history of diabetes or having chyle were eliminated, and 70 samples were measured as samples of healthy individuals. From the distribution of the measurements, the tentative cutoff value was set at average value plus 3 SD according to the non-parametric method (FIG. 7). As a result, the cutoff value was determined as 13.3 ng/mL.

Figure 8:
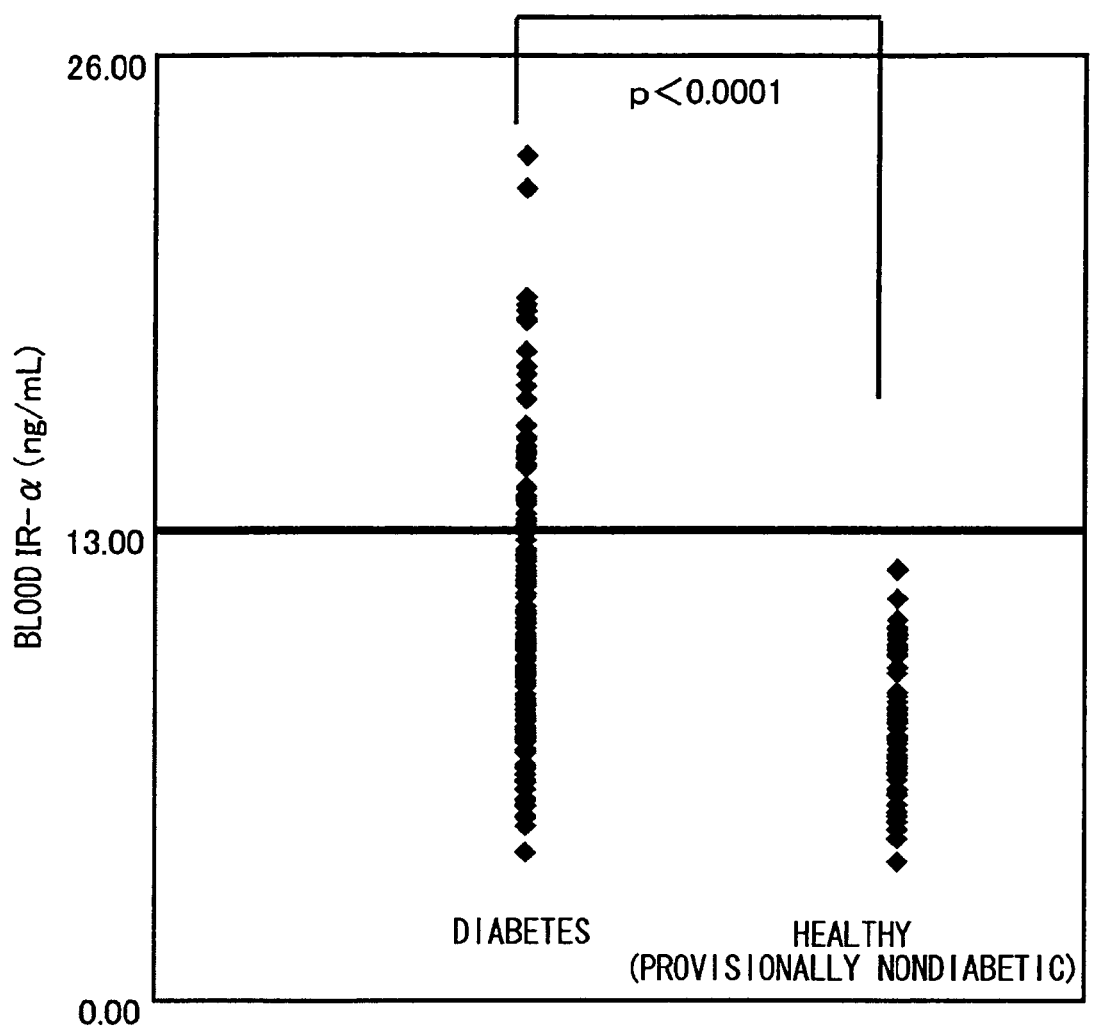
FIG. 8 shows the result of a significant difference test on the concentration of the insulin receptor α-subunit in blood (ng/mL) in diabetes patients and healthy individuals.

Next, at the University of Tokushima School of Medicine, 168 samples donated by diabetes patients with informed consent were measured (FIG. 8). As a result, the concentrations of insulin receptor α-subunit in the sera of diabetes patients were on average 10.7 ng/mL, the maximum value was 23.3 ng/mL, and a clear difference from healthy individuals was observed.

In view of the above, the value measured for the insulin receptor α-subunit in the blood was considered useful in the diagnosis of diabetes.

11. Measurement of Insulin Receptor α-subunit in the Sera of Cancer Patients

Figure 9:
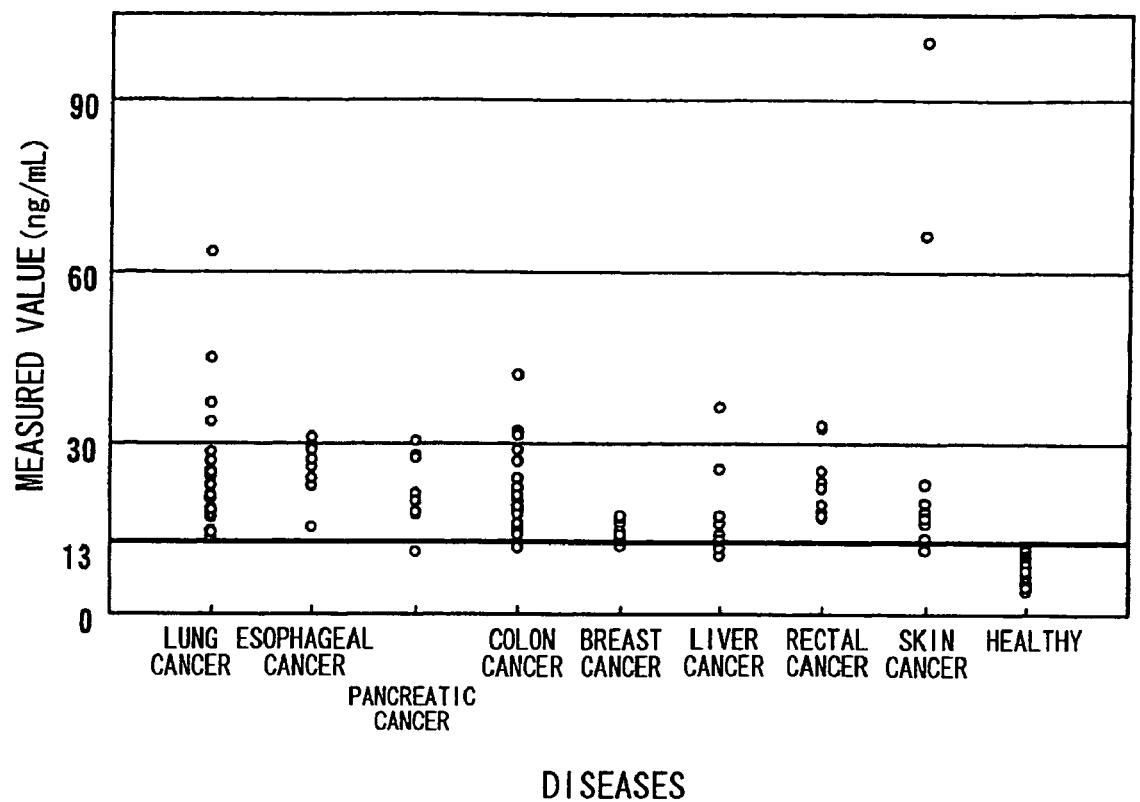
FIG. 9 shows the distribution of the insulin receptor α-subunit concentration in the sera of various cancer patients and healthy individuals. In the figure, the vertical axis indicates the measured values of the insulin receptor α-subunit concentration in the sera (ng/mL), and the horizontal axis indicates the type of disease (cancer).

Next, various cancer patient sera purchased from commercial suppliers were used as samples for the measurement of the insulin receptor α-subunit concentrations. The measured patient samples were ten samples each from lung cancer, esophageal cancer, pancreatic cancer, colon cancer, breast cancer, liver cancer, rectal cancer, and skin cancer patients. The results of the measurements are shown in Table 1 and FIG. 9. The concentrations of insulin receptor α-subunit in all types of cancers marked significantly higher values than those of healthy individuals. Therefore, measurement of the insulin receptor α-subunit in blood is considered to be useful for diagnosing cancer.

TABLE 1

|  | 13 ng/mL or more | Percent positive (%) |
| --- | --- | --- |
| Lung cancer | 20/20 | 100 |
| Esophageal cancer | 10/10 | 100 |
| Pancreatic cancer | 9/10 | 90 |
| Colon cancer | 19/20 | 95 |
| Breast cancer | 9/10 | 90 |
| Liver cancer | 6/10 | 60 |
| Rectal cancer | 10/10 | 100 |
| Skin cancer | 8/10 | 80 |
| Healthy individuals | 0/70 | 0 |

INDUSTRIAL APPLICABILITY

The present invention provides methods for measuring the free insulin receptor α-subunit in blood. The measured value of the free insulin receptor α-subunit in blood is useful as a diagnostic marker for diabetes. More specifically, when the measured value of the free insulin receptor α-subunit in blood is higher in a subject compared to that in a control, the subject is predicted to have diabetes or a risk factor for diabetes.

The present invention also provides novel methods for diagnosing cancer. The measured value of the free insulin receptor α-subunit in blood is useful as a diagnostic marker for cancer. More specifically, when the measured value of the free insulin receptor α-subunit in blood is higher in a subject compared to that in a control, the subject is predicted to have cancer. The measured values for the insulin receptor α-subunit were higher in patients suffering from cancers in a wide variety of organs than in healthy individuals. Therefore, the insulin receptor α-subunit can be used as a marker for any of several cancer types. More specifically, the present invention provides a novel broad-spectrum tumor marker.

The invention claimed is:

1. A method for diagnosing diabetes, wherein the method comprises the steps of:
   a) measuring the amount of a free insulin receptor α-subunit in a biological sample of a subject;
   b) comparing the amount of the free insulin receptor α-subunit with that of a control; and
   c) determining the subject to have diabetes when the amount of free insulin receptor α-subunit in the biological sample of the subject is greater than that of the control.

2. The method for diagnosis of claim 1, wherein the biological sample is a blood sample.

3. The method for diagnosis of claim 2, wherein the amount of the free insulin receptor α-subunit is measured by the steps of: (1) contacting a blood sample with an antibody recognizing the insulin receptor α-subunit; (2) detecting binding of said antibody to the insulin receptor α-subunit present in blood; and (3) determining the amount of free insulin receptor α-subunit in blood based on the level of binding detected between said antibody and subunit.

* * * * *

SEQUENCE LISTING

```
<160> NUMBER OF SEQ ID NOS: 2

<210> SEQ ID NO 1
<211> LENGTH: 2859
<212> TYPE: DNA
<213> ORGANISM: Homo sapiens
<220> FEATURE:
<221> NAME/KEY: sig_peptide
<222> LOCATION: (1)...(81)
<220> FEATURE:
<221> NAME/KEY: CDS
<222> LOCATION: (1)...(2859)
<220> FEATURE:
<221> NAME/KEY: mat_peptide
<222> LOCATION: (82)...(926)

<400> SEQUENCE: 1 atg ggc acc ggg ggc cgg cgg ggg gcg gcg gcc gcg ccg ctg ctg gtg      48
Met Gly Thr Gly Gly Arg Arg Gly Ala Ala Ala Ala Pro Leu Leu Val
            -25                 -20                 -15 gcg gtg gcc gcg ctg cta ctg ggc gcc gcg ggc cac ctg tac ccc gga      96
Ala Val Ala Ala Leu Leu Leu Gly Ala Ala Gly His Leu Tyr Pro Gly
        -10                  -5                   1               5 gag gtg tgt ccc ggc atg gat atc cgg aac aac ctc act agg ttg cat     144
Glu Val Cys Pro Gly Met Asp Ile Arg Asn Asn Leu Thr Arg Leu His
                 10                  15                  20 gag ctg gag aat tgc tct gtc atc gaa gga cac ttg cag ata ctc ttg     192
Glu Leu Glu Asn Cys Ser Val Ile Glu Gly His Leu Gln Ile Leu Leu
             25                  30                  35
```

-continued

```
atg ttc aaa acg agg ccc gaa gat ttc cga gac ctc agt ttc ccc aaa        240
Met Phe Lys Thr Arg Pro Glu Asp Phe Arg Asp Leu Ser Phe Pro Lys
         40                  45                  50 ctc atc atg atc act gat tac ttg ctg ctc ttc cgg gtc tat ggg ctc        288
Leu Ile Met Ile Thr Asp Tyr Leu Leu Leu Phe Arg Val Tyr Gly Leu
 55                  60                  65 gag agc ctg aag gac ctg ttc ccc aac ctc acg gtc atc cgg gga tca        336
Glu Ser Leu Lys Asp Leu Phe Pro Asn Leu Thr Val Ile Arg Gly Ser
 70                  75                  80                  85 cga ctg ttc ttt aac tac gcg ctg gtc atc ttc gag atg gtt cac ctc        384
Arg Leu Phe Phe Asn Tyr Ala Leu Val Ile Phe Glu Met Val His Leu
                 90                  95                 100 aag gaa ctc ggc ctc tac aac ctg atg aac atc acc cgg ggt tct gtc        432
Lys Glu Leu Gly Leu Tyr Asn Leu Met Asn Ile Thr Arg Gly Ser Val
            105                 110                 115 cgc atc gag aag aac aat gag ctc tgt tac ttg gcc act atc gac tgg        480
Arg Ile Glu Lys Asn Asn Glu Leu Cys Tyr Leu Ala Thr Ile Asp Trp
    120                 125                 130 tcc cgt atc ctg gat tcc gtg gag gat aat cac atc gtg ttg aac aaa        528
Ser Arg Ile Leu Asp Ser Val Glu Asp Asn His Ile Val Leu Asn Lys
135                 140                 145 gat gac aac gag gag tgt gga gac atc tgt ccg ggt acc gcg aag ggc        576
Asp Asp Asn Glu Glu Cys Gly Asp Ile Cys Pro Gly Thr Ala Lys Gly
150                 155                 160                 165 aag acc aac tgc ccc gcc acc gtc atc aac ggg cag ttt gtc gaa cga        624
Lys Thr Asn Cys Pro Ala Thr Val Ile Asn Gly Gln Phe Val Glu Arg
                170                 175                 180 tgt tgg act cat agt cac tgc cag aaa gtt tgc ccg acc atc tgt aag        672
Cys Trp Thr His Ser His Cys Gln Lys Val Cys Pro Thr Ile Cys Lys
            185                 190                 195 tca cac ggc tgc acc gcc gaa ggc ctc tgt tgc cac agc gag tgc ctg        720
Ser His Gly Cys Thr Ala Glu Gly Leu Cys Cys His Ser Glu Cys Leu
    200                 205                 210 ggc aac tgt tct cag ccc gac gac ccc acc aag tgc gtg gcc tgc cgc        768
Gly Asn Cys Ser Gln Pro Asp Asp Pro Thr Lys Cys Val Ala Cys Arg
215                 220                 225 aac ttc tac ctg gac ggc agg tgt gtg gag acc tgc ccg ccc ccg tac        816
Asn Phe Tyr Leu Asp Gly Arg Cys Val Glu Thr Cys Pro Pro Pro Tyr
230                 235                 240                 245 tac cac ttc cag gac tgg cgc tgt gtg aac ttc agc ttc tgc cag gac        864
Tyr His Phe Gln Asp Trp Arg Cys Val Asn Phe Ser Phe Cys Gln Asp
                250                 255                 260 ctg cac cac aaa tgc aag aac tcg cgg agg cag ggc tgc cac caa tac        912
Leu His His Lys Cys Lys Asn Ser Arg Arg Gln Gly Cys His Gln Tyr
            265                 270                 275 gtc att cac aac aac aag tgc atc cct gag tgt ccc tcc ggg tac acg        960
Val Ile His Asn Asn Lys Cys Ile Pro Glu Cys Pro Ser Gly Tyr Thr
    280                 285                 290 atg aat tcc agc aac ttg ctg tgc acc cca tgc ctg ggt ccc tgt ccc       1008
Met Asn Ser Ser Asn Leu Leu Cys Thr Pro Cys Leu Gly Pro Cys Pro
295                 300                 305 aag gtg tgc cac ctc cta gaa ggc gag aag acc atc gac tcg gtg acg       1056
Lys Val Cys His Leu Leu Glu Gly Glu Lys Thr Ile Asp Ser Val Thr
310                 315                 320                 325 tct gcc cag gag ctc cga gga tgc acc gtc atc aac ggg agt ctg atc       1104
Ser Ala Gln Glu Leu Arg Gly Cys Thr Val Ile Asn Gly Ser Leu Ile
                330                 335                 340 atc aac att cga gga ggc aac aat ctg gca gct gag cta gaa gcc aac       1152
Ile Asn Ile Arg Gly Gly Asn Asn Leu Ala Ala Glu Leu Glu Ala Asn
```

```
                     345                 350                 355
ctc ggc ctc att gaa gaa att tca ggg tat cta aaa atc cgc cga tcc    1200
Leu Gly Leu Ile Glu Glu Ile Ser Gly Tyr Leu Lys Ile Arg Arg Ser
        360                 365                 370 tac gct ctg gtg tca ctt tcc ttc ttc cgg aag tta cgt ctg att cga    1248
Tyr Ala Leu Val Ser Leu Ser Phe Phe Arg Lys Leu Arg Leu Ile Arg
375                 380                 385 gga gag acc ttg gaa att ggg aac tac tcc ttc tat gcc ttg gac aac    1296
Gly Glu Thr Leu Glu Ile Gly Asn Tyr Ser Phe Tyr Ala Leu Asp Asn
390                 395                 400                 405 cag aac cta agg cag ctc tgg gac tgg agc aaa cac aac ctc acc acc    1344
Gln Asn Leu Arg Gln Leu Trp Asp Trp Ser Lys His Asn Leu Thr Thr
            410                 415                 420 act cag ggg aaa ctc ttc ttc cac tat aac ccc aaa ctc tgc ttg tca    1392
Thr Gln Gly Lys Leu Phe Phe His Tyr Asn Pro Lys Leu Cys Leu Ser
                425                 430                 435 gaa atc cac aag atg gaa gaa gtt tca gga acc aag ggg cgc cag gag    1440
Glu Ile His Lys Met Glu Glu Val Ser Gly Thr Lys Gly Arg Gln Glu
                    440                 445                 450 aga aac gac att gcc ctg aag acc aat ggg gac aag gca tcc tgt gaa    1488
Arg Asn Asp Ile Ala Leu Lys Thr Asn Gly Asp Lys Ala Ser Cys Glu
455                 460                 465 aat gag tta ctt aaa ttt tct tac att cgg aca tct ttt gac aag atc    1536
Asn Glu Leu Leu Lys Phe Ser Tyr Ile Arg Thr Ser Phe Asp Lys Ile
470                 475                 480                 485 ttg ctg aga tgg gag ccg tac tgg ccc ccc gac ttc cga gac ctc ttg    1584
Leu Leu Arg Trp Glu Pro Tyr Trp Pro Pro Asp Phe Arg Asp Leu Leu
                490                 495                 500 ggg ttc atg ctg ttc tac aaa gag gcc cct tat cag aat gtg acg gag    1632
Gly Phe Met Leu Phe Tyr Lys Glu Ala Pro Tyr Gln Asn Val Thr Glu
                505                 510                 515 ttc gat ggg cag gat gcg tgt ggt tcc aac agt tgg acg gtg gta gac    1680
Phe Asp Gly Gln Asp Ala Cys Gly Ser Asn Ser Trp Thr Val Val Asp
                520                 525                 530 att gac cca ccc ctg agg tcc aac gac ccc aaa tca cag aac cac cca    1728
Ile Asp Pro Pro Leu Arg Ser Asn Asp Pro Lys Ser Gln Asn His Pro
535                 540                 545 ggg tgg ctg atg cgg ggt ctc aag ccc tgg acc cag tat gcc atc ttt    1776
Gly Trp Leu Met Arg Gly Leu Lys Pro Trp Thr Gln Tyr Ala Ile Phe
550                 555                 560                 565 gtg aag acc ctg gtc acc ttt tcg gat gaa cgc cgg acc tat ggg gcc    1824
Val Lys Thr Leu Val Thr Phe Ser Asp Glu Arg Arg Thr Tyr Gly Ala
                570                 575                 580 aag agt gac atc att tat gtc cag aca gat gcc acc aac ccc tct gtg    1872
Lys Ser Asp Ile Ile Tyr Val Gln Thr Asp Ala Thr Asn Pro Ser Val
                585                 590                 595 ccc ctg gat cca atc tca gtg tct aac tca tca tcc cag att att ctg    1920
Pro Leu Asp Pro Ile Ser Val Ser Asn Ser Ser Ser Gln Ile Ile Leu
                600                 605                 610 aag tgg aaa cca ccc tcc gac ccc aat ggc aac atc acc cac tac ctg    1968
Lys Trp Lys Pro Pro Ser Asp Pro Asn Gly Asn Ile Thr His Tyr Leu
615                 620                 625 gtt ttc tgg gag agg cag gcg gaa gac agt gag ctg ttc gag ctg gat    2016
Val Phe Trp Glu Arg Gln Ala Glu Asp Ser Glu Leu Phe Glu Leu Asp
630                 635                 640                 645 tat tgc ctc aaa ggg ctg aag ctg ccc tcg agg acc tgg tct cca cca    2064
Tyr Cys Leu Lys Gly Leu Lys Leu Pro Ser Arg Thr Trp Ser Pro Pro
                650                 655                 660 ttc gag tct gaa gat tct cag aag cac aac cag agt gag tat gag gat    2112
Phe Glu Ser Glu Asp Ser Gln Lys His Asn Gln Ser Glu Tyr Glu Asp
```

```
Phe Glu Ser Glu Asp Ser Gln Lys His Asn Gln Ser Glu Tyr Glu Asp
                665                 670                 675 tcg gcc ggc gaa tgc tgc tcc tgt cca aag aca gac tct cag atc ctg      2160
Ser Ala Gly Glu Cys Cys Ser Cys Pro Lys Thr Asp Ser Gln Ile Leu
        680                 685                 690 aag gag ctg gag gag tcc tcg ttt agg aag acg ttt gag gat tac ctg      2208
Lys Glu Leu Glu Glu Ser Ser Phe Arg Lys Thr Phe Glu Asp Tyr Leu
    695                 700                 705 cac aac gtg gtt ttc gtc ccc aga aaa acc tct tca ggc act ggt gcc      2256
His Asn Val Val Phe Val Pro Arg Lys Thr Ser Ser Gly Thr Gly Ala
710                 715                 720                 725 gag gac cct agg cca tct cgg aaa cgc agg tcc ctt ggc gat gtt ggg      2304
Glu Asp Pro Arg Pro Ser Arg Lys Arg Arg Ser Leu Gly Asp Val Gly
                730                 735                 740 aat gtg acg gtg gcc gtg ccc acg gtg gca gct ttc ccc aac act tcc      2352
Asn Val Thr Val Ala Val Pro Thr Val Ala Ala Phe Pro Asn Thr Ser
            745                 750                 755 tcg acc agc gtg ccc acg agt ccg gag gag cac agg cct ttt gag aag      2400
Ser Thr Ser Val Pro Thr Ser Pro Glu Glu His Arg Pro Phe Glu Lys
        760                 765                 770 gtg gtg aac aag gag tcg ctg gtc atc tcc ggc ttg cga cac ttc acg      2448
Val Val Asn Lys Glu Ser Leu Val Ile Ser Gly Leu Arg His Phe Thr
    775                 780                 785 ggc tat cgc atc gag ctg cag gct tgc aac cag gac acc cct gag gaa      2496
Gly Tyr Arg Ile Glu Leu Gln Ala Cys Asn Gln Asp Thr Pro Glu Glu
790                 795                 800                 805 cgg tgc agt gtg gca gcc tac gtc agt gcg agg acc atg cct gaa gcc      2544
Arg Cys Ser Val Ala Ala Tyr Val Ser Ala Arg Thr Met Pro Glu Ala
                810                 815                 820 aag gct gat gac att gtt ggc cct gtg acg cat gaa atc ttt gag aac      2592
Lys Ala Asp Asp Ile Val Gly Pro Val Thr His Glu Ile Phe Glu Asn
            825                 830                 835 aac gtc gtc cac ttg atg tgg cag gag ccg aag gag ccc aat ggt ctg      2640
Asn Val Val His Leu Met Trp Gln Glu Pro Lys Glu Pro Asn Gly Leu
        840                 845                 850 atc gtg ctg tat gaa gtg agt tat cgg cga tat ggt gat gag gag ctg      2688
Ile Val Leu Tyr Glu Val Ser Tyr Arg Arg Tyr Gly Asp Glu Glu Leu
    855                 860                 865 cat ctc tgc gtc tcc cgc aag cac ttc gct ctg gaa cgg ggc tgc agg      2736
His Leu Cys Val Ser Arg Lys His Phe Ala Leu Glu Arg Gly Cys Arg
870                 875                 880                 885 ctg cgt ggg ctg tca ccg ggg aac tac agc gtg cga atc cgg gcc acc      2784
Leu Arg Gly Leu Ser Pro Gly Asn Tyr Ser Val Arg Ile Arg Ala Thr
                890                 895                 900 tcc ctt gcg ggc aac ggc tct tgg acg gaa ccc acc tat ttc tac gtg      2832
Ser Leu Ala Gly Asn Gly Ser Trp Thr Glu Pro Thr Tyr Phe Tyr Val
            905                 910                 915 aca gac tat tta gac gtc ccg tca aat                                  2859
Thr Asp Tyr Leu Asp Val Pro Ser Asn
        920                 925

<210> SEQ ID NO 2
<211> LENGTH: 953
<212> TYPE: PRT
<213> ORGANISM: Homo sapiens
<220> FEATURE:
<221> NAME/KEY: SIGNAL
<222> LOCATION: (1)...(27)

<400> SEQUENCE: 2

Met Gly Thr Gly Gly Arg Arg Gly Ala Ala Ala Ala Pro Leu Leu Val
```

-continued

```
                -25                 -20                 -15
Ala Val Ala Ala Leu Leu Leu Gly Ala Ala Gly His Leu Tyr Pro Gly
        -10                  -5                   1                   5

Glu Val Cys Pro Gly Met Asp Ile Arg Asn Asn Leu Thr Arg Leu His
                     10                  15                  20

Glu Leu Glu Asn Cys Ser Val Ile Glu Gly His Leu Gln Ile Leu Leu
                 25                  30                  35

Met Phe Lys Thr Arg Pro Glu Asp Phe Arg Asp Leu Ser Phe Pro Lys
         40                  45                  50

Leu Ile Met Ile Thr Asp Tyr Leu Leu Leu Phe Arg Val Tyr Gly Leu
     55                  60                  65

Glu Ser Leu Lys Asp Leu Phe Pro Asn Leu Thr Val Ile Arg Gly Ser
 70                  75                  80                  85

Arg Leu Phe Phe Asn Tyr Ala Leu Val Ile Phe Glu Met Val His Leu
             90                  95                 100

Lys Glu Leu Gly Leu Tyr Asn Leu Met Asn Ile Thr Arg Gly Ser Val
                105                 110                 115

Arg Ile Glu Lys Asn Asn Glu Leu Cys Tyr Leu Ala Thr Ile Asp Trp
         120                 125                 130

Ser Arg Ile Leu Asp Ser Val Glu Asp Asn His Ile Val Leu Asn Lys
     135                 140                 145

Asp Asp Asn Glu Glu Cys Gly Asp Ile Cys Pro Gly Thr Ala Lys Gly
150                 155                 160                 165

Lys Thr Asn Cys Pro Ala Thr Val Ile Asn Gly Gln Phe Val Glu Arg
             170                 175                 180

Cys Trp Thr His Ser His Cys Gln Lys Val Cys Pro Thr Ile Cys Lys
                185                 190                 195

Ser His Gly Cys Thr Ala Glu Gly Leu Cys Cys His Ser Glu Cys Leu
         200                 205                 210

Gly Asn Cys Ser Gln Pro Asp Asp Pro Thr Lys Cys Val Ala Cys Arg
     215                 220                 225

Asn Phe Tyr Leu Asp Gly Arg Cys Val Glu Thr Cys Pro Pro Pro Tyr
230                 235                 240                 245

Tyr His Phe Gln Asp Trp Arg Cys Val Asn Phe Ser Phe Cys Gln Asp
             250                 255                 260

Leu His His Lys Cys Lys Asn Ser Arg Arg Gln Gly Cys His Gln Tyr
                265                 270                 275

Val Ile His Asn Asn Lys Cys Ile Pro Glu Cys Pro Ser Gly Tyr Thr
         280                 285                 290

Met Asn Ser Ser Asn Leu Leu Cys Thr Pro Cys Leu Gly Pro Cys Pro
     295                 300                 305

Lys Val Cys His Leu Leu Glu Gly Glu Lys Thr Ile Asp Ser Val Thr
310                 315                 320                 325

Ser Ala Gln Glu Leu Arg Gly Cys Thr Val Ile Asn Gly Ser Leu Ile
             330                 335                 340

Ile Asn Ile Arg Gly Gly Asn Asn Leu Ala Ala Glu Leu Glu Ala Asn
                345                 350                 355

Leu Gly Leu Ile Glu Glu Ile Ser Gly Tyr Leu Lys Ile Arg Arg Ser
         360                 365                 370

Tyr Ala Leu Val Ser Leu Ser Phe Phe Arg Lys Leu Arg Leu Ile Arg
     375                 380                 385

Gly Glu Thr Leu Glu Ile Gly Asn Tyr Ser Phe Tyr Ala Leu Asp Asn
390                 395                 400                 405
```

-continued

```
Gln Asn Leu Arg Gln Leu Trp Asp Trp Ser Lys His Asn Leu Thr Thr
            410                 415                 420

Thr Gln Gly Lys Leu Phe Phe His Tyr Asn Pro Lys Leu Cys Leu Ser
        425                 430                 435

Glu Ile His Lys Met Glu Glu Val Ser Gly Thr Lys Gly Arg Gln Glu
        440                 445                 450

Arg Asn Asp Ile Ala Leu Lys Thr Asn Gly Asp Lys Ala Ser Cys Glu
    455                 460                 465

Asn Glu Leu Leu Lys Phe Ser Tyr Ile Arg Thr Ser Phe Asp Lys Ile
470                 475                 480                 485

Leu Leu Arg Trp Glu Pro Tyr Trp Pro Pro Asp Phe Arg Asp Leu Leu
                490                 495                 500

Gly Phe Met Leu Phe Tyr Lys Glu Ala Pro Tyr Gln Asn Val Thr Glu
            505                 510                 515

Phe Asp Gly Gln Asp Ala Cys Gly Ser Asn Ser Trp Thr Val Val Asp
        520                 525                 530

Ile Asp Pro Pro Leu Arg Ser Asn Asp Pro Lys Ser Gln Asn His Pro
    535                 540                 545

Gly Trp Leu Met Arg Gly Leu Lys Pro Trp Thr Gln Tyr Ala Ile Phe
550                 555                 560                 565

Val Lys Thr Leu Val Thr Phe Ser Asp Glu Arg Arg Thr Tyr Gly Ala
                570                 575                 580

Lys Ser Asp Ile Ile Tyr Val Gln Thr Asp Ala Thr Asn Pro Ser Val
            585                 590                 595

Pro Leu Asp Pro Ile Ser Val Ser Asn Ser Ser Ser Gln Ile Ile Leu
        600                 605                 610

Lys Trp Lys Pro Pro Ser Asp Pro Asn Gly Asn Ile Thr His Tyr Leu
    615                 620                 625

Val Phe Trp Glu Arg Gln Ala Glu Asp Ser Glu Leu Phe Glu Leu Asp
630                 635                 640                 645

Tyr Cys Leu Lys Gly Leu Lys Leu Pro Ser Arg Thr Trp Ser Pro Pro
                650                 655                 660

Phe Glu Ser Glu Asp Ser Gln Lys His Asn Gln Ser Glu Tyr Glu Asp
            665                 670                 675

Ser Ala Gly Glu Cys Cys Ser Cys Pro Lys Thr Asp Ser Gln Ile Leu
        680                 685                 690

Lys Glu Leu Glu Glu Ser Ser Phe Arg Lys Thr Phe Glu Asp Tyr Leu
    695                 700                 705

His Asn Val Val Phe Val Pro Arg Lys Thr Ser Ser Gly Thr Gly Ala
710                 715                 720                 725

Glu Asp Pro Arg Pro Ser Arg Lys Arg Arg Ser Leu Gly Asp Val Gly
                730                 735                 740

Asn Val Thr Val Ala Val Pro Thr Val Ala Ala Phe Pro Asn Thr Ser
            745                 750                 755

Ser Thr Ser Val Pro Thr Ser Pro Glu Glu His Arg Pro Phe Glu Lys
        760                 765                 770

Val Val Asn Lys Glu Ser Leu Val Ile Ser Gly Leu Arg His Phe Thr
    775                 780                 785

Gly Tyr Arg Ile Glu Leu Gln Ala Cys Asn Gln Asp Thr Pro Glu Glu
790                 795                 800                 805

Arg Cys Ser Val Ala Ala Tyr Val Ser Ala Arg Thr Met Pro Glu Ala
                810                 815                 820
```

-continued

```
Lys Ala Asp Asp Ile Val Gly Pro Val Thr His Glu Ile Phe Glu Asn
            825                 830                 835

Asn Val Val His Leu Met Trp Gln Glu Pro Lys Glu Pro Asn Gly Leu
        840                 845                 850

Ile Val Leu Tyr Glu Val Ser Tyr Arg Arg Tyr Gly Asp Glu Glu Leu
    855                 860                 865

His Leu Cys Val Ser Arg Lys His Phe Ala Leu Glu Arg Gly Cys Arg
870                 875                 880                 885

Leu Arg Gly Leu Ser Pro Gly Asn Tyr Ser Val Arg Ile Arg Ala Thr
            890                 895                 900

Ser Leu Ala Gly Asn Gly Ser Trp Thr Glu Pro Thr Tyr Phe Tyr Val
            905                 910                 915

Thr Asp Tyr Leu Asp Val Pro Ser Asn
            920                 925
```